United States Patent
Wiets et al.

(10) Patent No.: US 11,229,411 B2
(45) Date of Patent: Jan. 25, 2022

(54) X-RAY APPARATUS INCLUDING X-RAY REFLECTOR AND METHOD FOR OPERATING THE X-RAY APPARATUS

(71) Applicant: Siemens Healthcare GmbH, Erlangen (DE)

(72) Inventors: Michael Wiets, Langensendelbach (DE); Philipp Wiets, Langensendelbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 104 days.

(21) Appl. No.: 16/526,186

(22) Filed: Jul. 30, 2019

(65) Prior Publication Data
US 2020/0043626 A1 Feb. 6, 2020

(30) Foreign Application Priority Data
Aug. 2, 2018 (EP) .................... 18187106

(51) Int. Cl.
*A61B 6/00* (2006.01)
*A61B 6/03* (2006.01)
(Continued)

(52) U.S. Cl.
CPC ............... *A61B 6/40* (2013.01); *A61B 6/032* (2013.01); *A61B 6/035* (2013.01); *A61B 6/04* (2013.01);
(Continued)

(58) Field of Classification Search
CPC ........... A61B 6/032; A61B 6/035; A61B 6/04; A61B 6/0407; A61B 6/0487; A61B 6/06;
(Continued)

(56) References Cited

U.S. PATENT DOCUMENTS

| | | | |
|---|---|---|---|
| 4,625,323 A | 11/1986 | Okaya | |
| 5,204,887 A | 4/1993 | Hayashida et al. | |

(Continued)

FOREIGN PATENT DOCUMENTS

| | | |
|---|---|---|
| DE | 10139384 A1 | 3/2003 |
| DE | 10304852 A1 | 8/2004 |

(Continued)

OTHER PUBLICATIONS

"Focusing research on XUV optics for industrial and scientific exploitation"; XUV Optics; Industrial Focus Group; University of Twente; PDF.

(Continued)

*Primary Examiner* — Allen C. Ho
(74) *Attorney, Agent, or Firm* — Harness, Dickey & Pierce, P.L.C.

(57) ABSTRACT

An X-ray apparatus includes an X-ray source embodied to generate X-rays; an X-ray detector; and an X-ray reflector. The X-ray reflector is embodied to reflect X-rays generated by the X-ray source such that the reflected X-rays hit the X-ray detector. The X-ray detector is in particular embodied to detect the X-rays. The X-ray apparatus can, on the one hand, enlarge the available space above a patient. Furthermore, focusing via the X-ray reflector enables the power of the X-ray source to be increased while retaining a constant spatial resolution or the spatial resolution to be improved while retaining a constant power of the X-ray source.

27 Claims, 7 Drawing Sheets

(51) Int. Cl.
*G21K 1/06* (2006.01)
*A61B 6/04* (2006.01)
*A61B 6/06* (2006.01)

(52) U.S. Cl.
CPC .............. *A61B 6/0407* (2013.01); *A61B 6/06* (2013.01); *A61B 6/4085* (2013.01); *A61B 6/4092* (2013.01); *A61B 6/4233* (2013.01); *A61B 6/4241* (2013.01); *A61B 6/4452* (2013.01); *A61B 6/482* (2013.01); *A61B 6/54* (2013.01); *G21K 1/062* (2013.01); *G21K 1/067* (2013.01); *G21K 2201/061* (2013.01); *G21K 2201/062* (2013.01)

(58) Field of Classification Search
CPC ......... A61B 6/40; A61B 6/405; A61B 6/4064; A61B 6/4078; A61B 6/4085; A61B 6/4092; A61B 6/42; A61B 6/4208; A61B 6/4233; A61B 6/4241; A61B 6/44; A61B 6/4429; A61B 6/4435; A61B 6/4441; A61B 6/4447; A61B 6/4452; A61B 6/482; G21K 1/06; G21K 1/062; G21K 1/067
USPC ............... 378/5, 16, 62, 82–85, 98.9, 98.11, 378/196–198
See application file for complete search history.

(56) References Cited

U.S. PATENT DOCUMENTS

| | | | |
|---|---|---|---|
| 5,672,211 A | 9/1997 | Mai | |
| 6,317,483 B1* | 11/2001 | Chen | B82Y 10/00 378/145 |
| 6,421,417 B1* | 7/2002 | Jiang | G02B 5/0883 378/84 |
| 6,668,040 B2* | 12/2003 | Cederstrom | G21K 1/06 378/84 |
| 7,187,753 B2* | 3/2007 | Freudenberger | G21K 1/06 378/115 |
| 9,390,881 B2* | 7/2016 | Yun | H01J 35/147 |
| 9,448,190 B2* | 9/2016 | Yun | G01N 23/2076 |
| 9,449,781 B2* | 9/2016 | Yun | G21K 1/06 |
| 9,594,036 B2* | 3/2017 | Yun | G21K 1/06 |
| 9,601,308 B2* | 3/2017 | Anan | G01N 23/2252 |
| 9,653,250 B2* | 5/2017 | Turyanskiy | H01J 35/116 |
| 9,658,174 B2* | 5/2017 | Omote | G01N 23/20016 |
| 9,820,705 B2* | 11/2017 | Kim | A61B 6/4417 |
| 10,145,808 B2* | 12/2018 | Omote | G21K 1/06 |
| 10,175,185 B2* | 1/2019 | Kawahara | G01N 23/207 |
| 10,295,485 B2* | 5/2019 | Yun | H01J 35/18 |
| 10,416,099 B2* | 9/2019 | Yun | G21K 1/06 |
| 10,429,326 B2* | 10/2019 | Hoffman | G01N 23/207 |
| 10,436,723 B2* | 10/2019 | Osakabe | G21K 1/04 |
| 10,809,625 B2* | 10/2020 | Enkisch | G03F 7/70316 |
| 10,859,520 B2* | 12/2020 | Takimoto | G21K 1/06 |
| 10,867,717 B2* | 12/2020 | Bajt | G01N 23/20008 |
| 10,876,978 B2* | 12/2020 | Ogata | G01N 23/20016 |
| 10,908,103 B2* | 2/2021 | Waldschlager | A61B 6/485 |
| 10,925,556 B2* | 2/2021 | Roessl | A61B 6/06 |
| 2002/0159561 A1 | 10/2002 | Cederstrom | |
| 2004/0218718 A1 | 11/2004 | Freudenberger et al. | |
| 2007/0030947 A1 | 2/2007 | Popescu | |
| 2014/0010348 A1 | 1/2014 | Tsujino | |

FOREIGN PATENT DOCUMENTS

| | | |
|---|---|---|
| DE | 10322137 A1 | 12/2004 |
| JP | H01201200 A | 8/1989 |
| JP | H025334 A | 1/1990 |
| JP | H0438500 A | 2/1992 |
| JP | 2000046759 A | 2/2000 |
| JP | 2000135211 A | 5/2000 |
| JP | 2003505677 A | 2/2003 |
| JP | 2014008361 A | 1/2014 |

OTHER PUBLICATIONS

"X-ray optics"; Wikipedia; version from Jan. 12, 2018; https://en.wikipedia.org/wiki/X-ray_optics.

"Ultrapraezise Roentgenspiegel"; in spectrum.de; article from Oct. 26, 1998; screenshot from Mar. 19, 2018.

"Monochromator"; Wikipedia; version from Feb. 3, 2018 https://en.wikipedia.org/wiki/Monochromator.

Dietsch, Reiner: "Multischichten für röntgenoptische Anwendungen"; in: Jahresbericht 2011; IWS Frauenhofer Institut Werkstoff- und Strahltechnik; S. 22-26; Germany; 2001.

Lieberherr, Martin: "Kaustiken am Parabolspiege!"; http://physik.li/beispiele/Parabelkaustik/index.htm; Germany; 2008; May 10, 2018.

Röntgenspiege!"; in spectrum.de; article from 1998; http://www.spektrum.de/lexikon/physik/roentgenspiegel/12551".

European Search Report for European Patent Application No. 18187106.2 (Form 1507N) dated Jan. 16, 2019.

Japanese Office Action and English translation thereof dated Dec. 1, 2020.

Japanese Office Action and English translation thereof dated Aug. 3, 2021.

* cited by examiner

X-RAY APPARATUS INCLUDING X-RAY REFLECTOR AND METHOD FOR OPERATING THE X-RAY APPARATUS

PRIORITY STATEMENT

The present application hereby claims priority under 35 U.S.C. § 119 to European patent application number EP 18187106.2 filed Aug. 2, 2018, the entire contents of which are hereby incorporated herein by reference.

FIELD

Embodiments of the invention generally relate to an x-ray apparatus and method for operating the x-ray apparatus.

BACKGROUND

X-ray apparatuses usually include an X-ray source and an X-ray detector arranged on opposite sides of a patient during X-ray imaging. For example, C-arm X-ray apparatuses are known with which the X-ray source and the X-ray detector are arranged on opposite ends of a C-shaped or semicircular arm ("C-arm" for short).

However, this arrangement restricts the space available between the patient and the X-ray source or between the patient and the X-ray detector. This small space can impede a physician in the performance of diagnostic and/or therapeutic methods requiring the assistance of an X-ray apparatus. This is in particular the case when a flat-panel detector is used as the X-ray detector or when the X-ray apparatus further comprises an image amplifier since such facilities restrict the available space still further. Examples of such diagnostic and/or therapeutic methods are found inter alia in the field of cardiology or heart surgery, for example during catheterization of the heart or during a transcatheter aortic valve implantation, ("TAVI" for short). To enlarge the available space, it is known to increase the distance between the X-ray source and the X-ray detector (the technical term for this distance is "source-image distance", "SID" for short), but this simultaneously reduces the spatial resolution.

Furthermore, modern X-ray sources, in particular high-power rotary anode X-ray tubes, use a plurality of emitters with which respective parameters such as X-ray voltage, pulse times and/or X-ray current (another technical term for "X-ray current" is "tube current") can be set. If high spatial resolution is required during X-ray imaging, it is usual to use a small emitter to achieve a small focus and hence high spatial resolution. The simultaneous use of a high X-ray current and/or short pulse times reduces the available service life of the respective emitter. Therefore, it is usually not possible to set certain parameter combinations on such emitters, for example combinations of a high X-ray current with a short pulse duration or a high pulse frequency can be excluded by the manufacturer. It is, therefore, known to use emitters with a larger spatial extension, but this results in reduced spatial resolution.

In addition to medical imaging, X-ray apparatuses are also used for non-destructive material testing where problems similar to those during medical use can occur.

SUMMARY

Embodiments of the present invention provide an X-ray apparatus that provides a greater space between the examination volume and the X-ray detector or X-ray source without any deterioration of the spatial resolution and which further enables the use of emitters with a high spatial extension without any deterioration of the spatial resolution. Herein, examination volume means a region or volume that is to undergo an imaging examination by way of X-rays (for example a region of a patient or a region of a material or component to be tested).

Embodiments are directed to an X-ray apparatus and a method for operating an X-ray apparatus. Advantageous developments are described in the claims and in the description.

Features, advantages or alternative embodiments may also be transferred to the other claimed subject matter and vice versa. In other words, the substantive claims (which are, for example, directed at an apparatus) can also be developed with the features described or claimed in connection with a method. Herein, the corresponding functional features of the method are formed by corresponding substantive modules.

At least one embodiment of the invention is directed to an X-ray apparatus including an X-ray source embodied to generate X-rays further including an X-ray detector and further including an X-ray reflector, wherein the X-ray reflector is embodied to reflect X-rays generated by the X-ray source such that the X-rays hit the X-ray detector. In particular, the X-ray detector is embodied to detect the X-rays.

An embodiment of the invention furthermore relates to an X-ray apparatus, comprising:
an X-ray source embodied to generate X-rays;
an X-ray detector; and
an X-ray reflector, embodied to reflect X-rays generated by the X-ray source such that reflected X-rays hit the X-ray detector.

An embodiment of the invention furthermore relates to a method for operating an X-ray apparatus according to one of the embodiments of the invention. The method for operating the X-ray apparatus is based on the fact that an examination region is received, in particular received via an interface of a control system. The method is furthermore based on the fact that a position and/or an orientation of the X-ray reflector are set, in particular set via a computing unit of the control system, so that the X-rays reflected by the X-ray reflector irradiate the examination region. The method is furthermore based on the fact that X-rays are generated via the X-ray source and that X-rays are detected via the X-ray detector. The method for operating an X-ray apparatus is in particular a computer-implemented method. The method can also be embodied such that the generation of the X-rays via the X-ray source and the detection of the X-rays via the X-ray detector can be replaced by the method step of the generation of a control command for the generation of X-rays.

An embodiment of the invention furthermore relates to a method for operating an X-ray apparatus, comprising:
receiving an examination region;
first setting of at least one of a position and an orientation of an X-ray reflection unit of the X-ray apparatus so that the X-rays reflected by the X-ray reflector irradiate the examination region,
generating X-rays via the X-ray source; and
detecting the X-rays via the X-ray detector.

An embodiment of the invention can also relate to a control system for an X-ray apparatus according to an embodiment of the invention, including
an interface embodied to receive an examination region, furthermore embodied to provide a control command,
a computing unit embodied for the first setting of a position and/or an orientation of the X-ray reflector so that the X-rays reflected by the X-ray reflector irradiate the examination region, furthermore embodied to generate the control command to trigger X-rays via an X-ray source.

An embodiment of the invention can also relate to a computer program product with a computer program which can be loaded directly into a memory of a control system with program segments for executing all the steps of the method for operating an X-ray apparatus and/or embodiments thereof when the program segments are executed by the control system. The invention can furthermore also relate to a computer-readable storage medium on which program segments that can be read and executed by a control system are stored in order to execute all the steps of an embodiment of the method for operating an X-ray apparatus and/or embodiments thereof when the program segments are executed by the control system.

An embodiment of the invention can also relate to a non-transitory computer-readable medium, storing program segments downloadable and executable by a processor, to perform the method of an embodiment, when the program segments are executed by the processor.

BRIEF DESCRIPTION OF THE DRAWINGS

The above-described properties, features and advantages of this invention and also the manner in which they are achieved will become clearer and more plainly comprehensible in conjunction with the following description of the example embodiments explained in more detail in conjunction with the drawings. This description does not restrict the invention to these example embodiments. In different figures, the same components are given identical reference numbers. The figures are not generally true to scale and show.

DETAILED DESCRIPTION OF THE EXAMPLE EMBODIMENTS

Figure 1:
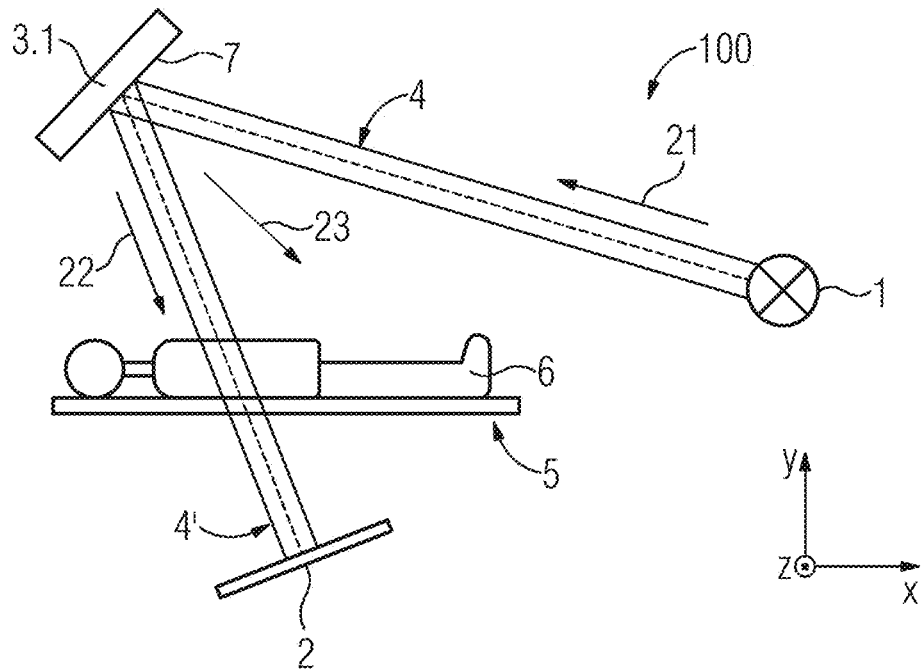
FIG. 1 a first example embodiment of an X-ray apparatus.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is directed to an X-ray apparatus including an X-ray source embodied to generate X-rays further including an X-ray detector and further including an X-ray reflector, wherein the X-ray reflector is embodied to reflect X-rays generated by the X-ray source such that the X-rays hit the X-ray detector. In particular, the X-ray detector is embodied to detect the X-rays.

The inventors have recognized that the use of an X-ray reflection facility means the X-ray source does not have to be placed on the straight line connecting an examination region and the X-ray detector. As a result, it is possible to provide a larger space between the examination volume and the X-ray detector or X-ray source without impairing the spatial resolution.

According to a further embodiment of the invention, the X-rays are propagated between the X-ray source and the X-ray reflector along a first direction, furthermore the X-rays are propagated between the X-ray reflector and the X-ray detector along a second direction, wherein the first direction is different from the second direction. Herein, the first direction can in particular be referred to as the incidence direction, the X-rays that are propagated along the first direction can in particular be referred to as incident radiation or incident X-rays. Herein, the second direction can in particular also be referred to as the exit direction, the X-rays that are propagated along the second direction X-rays can in particular be referred to as exiting radiation or as exiting X-rays or as reflected radiation or as reflected X-rays.

The first direction can also be referred to as the first propagation direction, the second direction can also be referred to as the second propagation direction. Particularly preferably the angle between the first direction and the second direction is smaller than 90° (i.e. particularly preferably the angle between the negative first direction and the second direction is greater than 90°), particularly preferably the angle between the first direction and the second direction is smaller than 60° (i.e. particularly preferably the angle between the negative first direction and the second direction is greater than 120°), and particularly preferably the angle between the first direction and the second direction is smaller than 30° (i.e. particularly preferably the angle between the negative first direction and the second direction is greater than 150°).

A direction can in particular be a three-dimensional vector, a straight line in three-dimensional space and/or the direction vector of a straight line in three-dimensional space. The angle $\alpha$ between two directions or two direction vectors $v_1$ and $v_2$ is defined by $\alpha = \arccos(v_1 \cdot v_2)$, wherein $v_1 \cdot v_2$ designates the scalar product of the vectors $v_1$ and $v_2$.

X-rays are propagated along a direction defined by a three-dimensional vector v when the X-rays are propagated within a rotating cone with an arbitrary apex, wherein the axis of the rotating cone is a straight line through the apex with the direction vector v and wherein the aperture angle of the rotating cone is smaller than 20°, in particular smaller than 5°, in particular smaller than 2.5° or in particular smaller than 1°. X-rays that are propagated within such a rotating cone are referred to as "fan-shaped" or "cone-shaped" X-rays. In particular, the sectional area of fan-shaped or cone-shaped X-rays with a plane orthogonal to the three-dimensional vector v is longer along the propagation direction. X-rays are also propagated along a direction defined by a three-dimensional vector v when the beams of the X-rays are propagated parallel to the direction v, in particular as a bundle of X-ray beams that are each parallel to the direction v. X-rays that are propagated parallel to a direction v are also referred to as "parallel" X-rays. In particular, the sectional area of parallel X-rays with a plane orthogonal to the three-dimensional vector v is approximately constant along the propagation direction.

The inventors have recognized that such a first and second direction of propagation enables a particularly large space to be provided between the examination volume and the X-ray detector or X-ray source.

According to a further embodiment of the invention, the X-ray detector is arranged orthogonally to the second direction. Another word for "orthogonal" is "perpendicular". An X-ray detector is in particular arranged orthogonally to the second direction when a detection layer of the X-ray detector is arranged orthogonally to the second direction. If the X-ray detector is a flat-panel detector including individual pixels, the X-ray detector is in particular arranged orthogonally to the second direction when the pixels are arranged in a grid-like layout with respect to a first grid direction and a second grid direction, wherein the first grid direction and the second grid direction are different and wherein both the first grid direction and the second grid direction are orthogonal to the second direction.

Two directions are in particular called orthogonal when they enclose an angle between 80° and 100°, in particular when they enclose an angle between 85° and 95°, in particular when they enclose an angle between 89° and 91°, and in particular when they enclose an angle of 90°. A plane is in particular orthogonal to a direction when each vector or each straight line in this plane is orthogonal to the direction. Two directions are in particular called parallel when they enclose an angle of less than 10° or of more than 170°, in particular when they enclose an angle of less than 5° or more than 175°, in particular when they enclose an angle of less than 1° or more than 179°, and in particular when they enclose a vector of exactly 0° or exactly 180°. If $v_1$ designates the three-dimensional vector of the first direction and $v_2$ the three-dimensional vector of the second direction, the first direction and the second direction in particular enclose an angle $\varphi$ where $\varphi = \arccos(v_1 \cdot v_2 / |v_1||v_2|)$, wherein $v_1 \cdot v_2$ designates the scalar product of the vectors $v_1$ and $v_2$, and $|v_1|$ and $|v_2|$ designates the value or length of the vector $v_1$ or $v_2$.

The inventors have recognized that X-rays that are orthogonally incident on the X-ray detector can be detected particularly efficiently with the X-ray detector.

According to a further embodiment of the invention, the X-ray reflection facility is arranged orthogonally to a third direction, wherein the third direction is a bisector of the negative first direction and the second direction.

A third direction is a bisector of the negative first direction and the second direction when the vector or the direction vector of the third direction lies in the plane spanned by the first direction and by the second direction (in other words when the first direction, the second direction and the third direction are linearly dependent), and when the negative first direction and the third direction enclose an angle that is equal to the angle enclosed by the second direction and the third direction. In particular, the third direction $v_3$ can be calculated as $v_3 = -v_1/|v_1| + v_2/|v_2|$.

The X-ray reflection facility is in particular arranged orthogonally to a third direction when a side of the X-ray reflection facility is arranged orthogonally to the third direction. The side of the X-ray reflection facility is in particular orthogonal to the third direction when this side and/or the X-ray reflection facility are rotationally symmetrical with respect to the third direction.

The inventors have recognized that the use of an X-ray reflection facility orthogonal to the bisector results in a particularly high proportion of the X-rays being reflected in the second direction.

According to a further embodiment of the invention, the X-ray reflector is embodied to focus the X-rays. The X-ray reflection facility is in particular embodied to focus the X-rays when the X-rays between the X-ray source and the X-ray reflection facility are cone-shaped X-rays and the X-rays between the X-ray reflection facility and the X-ray detector are parallel X-rays. In particular, in this case, starting from the X-ray reflection facility, the apex of the cone-shaped X-rays lies on the side specified by the negative first direction or in the half-space specified by the negative direction, in particular within the X-ray source.

The X-ray reflection facility is in particular furthermore embodied to focus the X-rays when the X-rays are parallel X-rays between the X-ray source and the X-ray reflection facility, and cone-shaped X-rays between the X-ray reflection facility and the X-ray detector. In particular, in this case, the apex of the cone-shaped X-rays lies on the side specified by the second direction side or in the half-space specified by the second direction, starting from the X-ray reflection facility.

The X-ray reflection facility is in particular furthermore embodied to focus the X-rays when the X-rays are first cone-shaped X-rays between the X-ray source and the X-ray reflection facility, and second cone-shaped X-rays between the X-ray reflection facility and the X-ray detector. In particular, in this case, starting from the X-ray reflection facility, the apex of the first cone-shaped X-rays lies on the side specified by the negative first direction or in the half-space specified by the negative direction, in particular within the X-ray source. In particular, in this case the apex of the second cone-shaped X-rays lies on the side specified by the second direction or in the half-space specified by the second direction, starting from the X-ray reflection facility.

The X-ray reflection facility can in particular also be configured to focus X-rays when the X-ray reflection facility includes a diaphragm, in particular a pinhole diaphragm. Herein, the pinhole diaphragm is in particular arranged in the beam path of the X-rays along the second direction.

The inventors have recognized that such an X-ray reflector enables the use of X-ray emitters with a large spatial extension without impairing the spatial image resolution, since the X-rays emitted by these extended emitters can be focused. X-ray emitters with a large spatial extension can in particular emit a higher X-ray power than X-ray emitters with a small extension. Furthermore, reflection at the X-ray reflector enables the generation of parallel X-rays that are more suitable for imaging than cone-shaped X-rays.

Furthermore, a focusing X-ray reflector means the focusing of the X-rays does not have to performed by the actual X-ray tube. Therefore, it is, for example, possible in a very cost-effective way to achieve different degrees of focusing with which in each case the same X-ray source but X-ray reflectors with different focusing strengths are used. Alternatively, the structure can also achieve different degrees of focusing in that the distance between the X-ray reflector and the X-ray detector is changed.

According to a further embodiment of the invention, the X-ray reflector comprises a concave side, wherein the concave side is embodied to reflect X-rays generated by the X-ray source. In particular, the concave side can have a parabolic shape. In particular, the X-ray source can be arranged in the apex of the parabolic side.

In particular, the curvature of the concave side can be embodied such that cone-shaped X-rays are reflected as parallel X-rays. In particular, to this end, the concave side can be embodied as a rotationally parabolic or as approximately rotationally parabolic. In particular, the shape of the concave side can also be defined by the solution to a differential equation. In particular, non-parallel parts of the X-rays can be filtered out along the second direction via a diaphragm, in particular a pinhole diaphragm.

A side is in particular a concave side when sections between two arbitrary points of the side do not intersect the X-ray reflector or only intersect the X-ray reflector at the edge. In particular, therefore, a partially linear or partially flat side can also be a concave side. In particular, a side is a concave side when the mathematical description of the side as a curved surface in space is concave. A concave side can in particular be concave with respect to only one first axis in particular when it is not curved with respect to a second axis that is orthogonal to the first axis. However, a concave side can also in particular be concave with respect to a first axis and a second axis, wherein the first axis differs from the second axis. In other words, the concave side is then curved with respect to the first axis and the second axis; such a curved side can also be referred to as "toroidal".

The inventors have recognized that an X-ray reflector with a concave side is particularly suitable for focusing X-rays.

According to a further embodiment of the invention, the X-ray reflector of the X-ray apparatus includes a coated mirror and/or a multi-layer mirror and/or a crystal monochromator. In particular, herein, the X-ray source is embodied to generate monochromatic X-rays. In particular, a crystal monochromator can be embodied to reflect X-rays by way of Bragg reflection. Herein, the coated mirror, the multi-layer mirror and/or the crystal monochromator can be embodied as concave, furthermore, the coated mirror, the multi-layer mirror and/or the crystal monochromator can be arranged on the concave side of the X-ray reflector. In particular, the coated mirror can be a metal-coated mirror.

In the case of a coated mirror, the X-ray reflector is in particular arranged or embodied such that the X-rays hit the X-ray reflector with a grazing incidence. Herein, the reflectivity of the coated mirror increases as the angle between the negative first direction and the normal of the X-ray reflector. In particular, this can result in total reflection as soon as the angle between the negative first direction and the normal of the X-ray reflector exceeds the total reflection angle. In particular, it is also possible for the X-ray reflector to comprise a plurality of interleaved coated mirrors, in particular in a Wolter arrangement, which can be used in X-ray telescopes. Herein, the interleaved coated mirrors can in particular be embodied as rotation paraboloids and/or as rotation hyperboloids.

A multi-layer mirror in particular includes two materials with different refractive indices arranged in alternating layers. In this application, "crystal monochromator" can be used as a synonym for the term "crystal lattice".

When using coated mirrors and/or multi-layer mirrors, it is advantageous to use coated mirrors and/or multi-layer mirrors with a low degree of roughness. The roughness in particular corresponds to the average distance between surface anomalies or superficial errors in the coated mirror and/or the multi-layer mirror, which cause diffuse scatter of the incident X-rays, or the average magnitude thereof. If the average distance or the degree of unevenness is much less than the wavelength, the surface roughness is of little significance. If, however, the value of this distance is of a similar order of magnitude as the wavelength of the light, an incident beam is mainly diffusely scattered and hardly reflected as a beam.

The inventors have recognized that the use of a coated mirror, a multi-layer mirror and/or a crystal monochromator enables X-rays to be reflected particularly efficiently. Herein, efficient reflection in particular means that the ratio of the intensity of the X-rays after reflection to the intensity of the X-rays before reflection is particularly high.

According to a further embodiment of the invention, the X-ray-reflection apparatus includes a Fresnel zone plate and/or a refractive X-ray lens. In particular, the X-ray apparatus can include a Fresnel zone plate and/or a refractive X-ray lens in that the X-ray reflector includes a Fresnel zone plate and/or a refractive X-ray lens. In particular, the X-ray reflector can be embodied as a Fresnel zone plate or as a refractive X-ray lens. A generic term for a Fresnel zone plate and/or refractive X-ray lens is "X-ray focusing unit". According to a further embodiment of the invention therefore, the X-ray apparatus includes an X-ray focusing unit, wherein the X-ray focusing unit is in particular embodied as a Fresnel zone plate and/or as a refractive X-ray lens.

A Fresnel zone plate includes in particular a plate on which a plurality of concentric rings that differ with respect to their transparency and/or their optical wavelength are arranged. This in particular enables X-rays to be diffracted on the annular gap structures and amplified due to constructive interference in the focal points. Alternatively or additionally, the selection as a ring of a transparent material with a thickness which effects a phase shift of the X-rays by 180° also achieves constructive interference in the focal points. Alternative terms for a Fresnel zone plate are "zone lenses", "diffractive lenses" or "kinoform lenses".

A Fresnel zone plate can in particular include a substrate with layers applied thereon, wherein individual layers can in particular only be applied over a partial region of the substrate and wherein in particular individual layers can include different materials. Such layers can in particular be vapor-deposited, alternatively it is also possible to use photolithographic methods. In particular silicon can be used as a substrate In the case of a refractive X-ray lens, the direction of the X-rays is changed by refraction at the interfaces between materials with different refractive indices (as described by Snell's law). In the case of X-light, the difference of the refractive index to one is referred to as the refractive index decrement. Since the refractive index decrement for X-ray light is only slightly below zero for all materials, a refractive X-ray lens in particular includes a plurality (in particular more than 10, in particular more than 100) individual lens elements with very small radii of curvature aligned in series in order to obtain a focal length of less than a meter (a technical term for such refractive lenses is "compound refractive lenses"). In the case of visible light, the refractive index of lens materials is markedly more than one and focusing lenses are thicker in their center than at their edges resulting in a typically biconvex shape. Since the refractive index for X-ray light is less than one, X-ray focusing lens are thinner at the center than at their edges, i.e. they have a biconcave shape. In particular, a parabolic shape of the refracting surfaces is very suitable for focusing X-ray light incident to the optical axis.

The inventors have recognized that the user of a Fresnel zone plate and/or a refractive X-ray lens enables particularly strong focusing of X-rays.

According to a further embodiment of the invention, the X-ray reflector includes a multi-layer mirror, wherein the X-rays are monochromatic and wherein the layer thickness of the multi-layer mirror is matched to the wavelength of the monochromatic X-rays. Herein, it is in particular not essential for the X-rays to be monochromatic, in other words the layer thickness of the multi-layer mirror is then matched to the wavelength of the X-rays. In particular, the layer thickness of the multi-layer mirror is simultaneously matched to the wavelength of the X-rays and to an angle of incidence of the X-rays. In particular, the angle of incidence is the angle between the negative first direction and the third direction.

The layer thickness of the multi-layer mirror is matched to the wavelength and/or the angle of incidence of the X-rays when the layer thickness, the wavelength and/or the angle of incidence satisfy the Bragg condition for constructive interference. Herein, in particular when the X-rays have several wavelengths, the layer thickness, the wavelength of the X-rays and/or the angle of incidence satisfy the Bragg condition for constructive interference when the layer thickness, one of the wavelengths of the X-rays and/or the angle of incidence satisfy the Bragg condition for constructive interference. In particular, the wavelength or wavelengths of the X-rays can be between 8 pm and 50 pm.

Herein, the angle of incidence of electromagnetic radiation, in particular of X-rays, is defined as the angle between the incidence direction or the exit direction and the line perpendicular to the plane of reflection (or the line perpendicular to the X-ray reflector or the line perpendicular to the side of the X-ray reflector). Equivalently, the angle of incidence can be defined as the smallest angle between the incidence direction or the exit direction and the plane of reflection (or the X-ray reflector or the side of the X-ray reflector).

The inventors have recognized that the use of a multi-layer mirror with a matched wavelength enables the X-rays to be reflected particularly efficiently.

According to a further embodiment of the invention, the X-ray source is embodied to emit light in the optically visible spectrum along the first direction. Herein, the X-ray reflector is embodied to reflect the light emitted by the X-ray source in the optical spectrum.

The X-ray source can in particular be embodied to emit light in the optically visible spectrum along the first propagation direction in that the X-ray source includes a deflection system, wherein the deflection system includes a mirror embodied to reflect light in the optically visible spectrum, wherein the mirror is transparent to X-rays. The X-ray reflector is in particular embodied to reflect the light emitted by the X-ray source in the optically visible spectrum in that the X-ray reflector includes a first reflection unit and a second reflection unit, wherein the first reflection unit is embodied to reflect X-rays, wherein the second reflection unit is embodied to reflect light in the optically visible spectrum and wherein the second reflection unit is transparent to X-rays.

Light in the optically visible spectrum is in particular electromagnetic radiation with a wavelength of between 380 nm and 780 nm. In particular, light in the optically visible spectrum can be laser light.

An object is in particular transparent to X-rays when, after passing through the object, the intensity of the X-rays is at least 90%, in particular at least 95%, and in particular at least 99% of the intensity of the X-rays before passing through the object.

The inventors have recognized that the reflecting arrangement of the X-ray source, X-ray reflector and X-ray detector makes it difficult to determine the spatial propagation of the X-rays or the volume of space penetrated by the X-rays. As a result, it is much easier for operators to be exposed to X-rays. The additional use of light in the optically visible spectrum enables the course of the X-rays to be visualized and safety of operation to be improved. Furthermore, the light in the optically visible spectrum can be used to position a patient. The use of deflection facilities enables actual X-ray sources to be combined inexpensively with light sources in the optically visible medium.

According to a further embodiment of the invention, the X-ray apparatus furthermore includes a patient support apparatus, wherein the patient support apparatus can be arranged in the beam path of the X-rays between the X-ray reflection facility and the X-ray detector.

The inventors have recognized that such an arrangement of the patient bench enables a particularly large space to be provided between the examination volume and the X-ray detector or X-ray source.

According to a further embodiment of the invention, the X-ray reflection facility and the X-ray detector can be rotated simultaneously about a common first axis of rotation. In particular, the X-ray reflection facility and the X-ray detector can in each case be attached to a common structure, wherein the common structure can be rotated about the first axis of rotation. In particular, the X-ray reflection facility and the X-ray detector can furthermore be jointly rotated about a third axis of rotation, wherein the third axis of rotation is orthogonal to the first axis of rotation. In particular, the common structure can be rotated about the third axis of rotation. The common structure can in particular be a C-arm. In particular, the X-ray source can be arranged along the first axis of rotation and in particular the X-ray source can be shiftable along the first axis of rotation and/or rotatable with respect to the first axis of rotation.

Two objects can in particular be rotated simultaneously about an axis of rotation when, during the rotation of the two objects about the axis of rotation, the relative angle of the first object to the axis of rotation and the second object to the axis of rotation is and/or remains constant.

The inventors have recognized that such an arrangement of an X-ray reflection facility and X-ray detector enables an examination volume to be imaged from different directions. In particular, this also enables three-dimensional and/or four-dimensional image data of the examination region to be recorded or reconstructed.

According to a further embodiment of the invention, the X-ray source and the X-ray reflection facility can be rotated simultaneously about a common second axis of rotation. In particular, the X-ray source and the X-ray reflection facility can in each case be fastened to a common structure, wherein the common structure can be rotated about the second axis of rotation. The first axis of rotation and the second axis of rotation can in particular be identical, furthermore, the first axis of rotation and the second axis of rotation can in particular be parallel, furthermore, the first axis of rotation and the second axis of rotation can have exactly one common point (in other words, the first axis of rotation intersects the second axis of rotation). However, it is also possible for the first axis of rotation and the second axis of rotation to be skew to one another.

The inventors have recognized that an X-ray reflection facility and X-ray source arranged in this way enables an examination volume to be imaged particularly efficiently from different directions.

According to a further possible embodiment of the invention, the X-ray reflector and the X-ray source are arranged on and/or in a common structure. According to a further possible embodiment of the invention, the X-ray reflector and the X-ray detector are arranged on and/or in a common structure. According to a further possible embodiment of the invention, the X-ray reflector, the X-ray detector and the X-ray source are arranged on and/or in a common structure. In particular, the common structure is embodied to rotate about at least one axis of rotation. In particular, the common structure can be a C-arm of a C-arm X-ray device, however the common structure can also be a gantry of a computed tomography scanner.

The inventors have recognized that the arrangement on and/or in a common structure renders the X-ray apparatus particularly stable with respect to external, in particular mechanical, influences and fewer movable axes have to be provided to change the position and/or orientation of the X-ray source, the X-ray detector and/or the X-ray reflector than is the case with an arrangement without a common structure and therefore the X-ray source, the X-ray detector and/or the X-ray reflector can in particular also be produced more cost-effectively.

The X-ray apparatuses according to the invention and their embodiments can in particular be used for medical imaging and/or for non-destructive material testing.

An embodiment of the invention furthermore relates to a method for operating an X-ray apparatus according to one of the embodiments of the invention. The method for operating the X-ray apparatus is based on the fact that an examination region is received, in particular received via an interface of a control system. The method is furthermore based on the fact that a position and/or an orientation of the X-ray reflector are set, in particular set via a computing unit of the control system, so that the X-rays reflected by the X-ray reflector irradiate the examination region. The method is furthermore based on the fact that X-rays are generated via the X-ray source and that X-rays are detected via the X-ray detector. The method for operating an X-ray apparatus is in particular a computer-implemented method. The method can also be embodied such that the generation of the X-rays via the X-ray source and the detection of the X-rays via the X-ray detector can be replaced by the method step of the generation of a control command for the generation of X-rays.

The inventors have recognized that this method is particularly suitable for operating an X-ray apparatus efficiently according to an embodiment of the invention.

An embodiment of the invention can also relate to a method for operating an X-ray apparatus according to an embodiment of the invention, wherein a position and/or an orientation of the X-ray reflector of the X-ray apparatus are set such that the X-rays reflected by the X-ray reflector irradiate a specified examination region.

According to a further embodiment of the method for operating the X-ray apparatus, the position and/or the orientation of the X-ray reflector is set such that an angle of reflection of the X-rays corresponds to a specified angle of reflection. Herein, the angle of reflection of the X-rays is in particular the angle of reflection of the X-rays with respect to the X-ray reflection facility. In particular, the angle of reflection is the angle between the negative first direction and the third direction, and/or the angle between the second direction and the third direction.

In particular, the method can be furthermore based on the fact that a wavelength of the X-rays is received and that the specified angle of reflection is determined based on the wavelength of the X-rays. In particular, the specified angle of reflection can be determined such that the Bragg condition is satisfied.

The inventors have recognized that setting a fixed angle of reflection enables X-ray reflectors to be operated with optimum reflection efficiency.

According to a further embodiment of the invention, the method for operating an X-ray apparatus furthermore includes a second setting of a position and/or an orientation of the X-ray detector so that the X-ray detector is arranged orthogonally to the X-rays reflected by the X-ray reflector.

The inventors have recognized that such a setting enables the X-ray detector to detect X-rays particularly efficiently since the efficiency of an X-ray detector is usually greatest with orthogonal incidence. The higher detection efficiency of the X-ray detector enables a patient's exposure to radiation to be minimized while retaining a constant image quality.

An embodiment of the invention can also relate to a control system for an X-ray apparatus according to an embodiment of the invention, including an interface embodied to receive an examination region, furthermore embodied to provide a control command, a computing unit embodied for the first setting of a position and/or an orientation of the X-ray reflector so that the X-rays reflected by the X-ray reflector irradiate the examination region, furthermore embodied to generate the control command to trigger X-rays via an X-ray source.

Such a control system can in particular be embodied to execute the above-described method according to the invention and its embodiments. The control system is embodied to execute this method and the embodiments thereof in that the interface and the computing unit are embodied to execute the corresponding method steps. The control system can in particular be part of the X-ray apparatus, in particular the control system can also be embodied to communicate with the X-ray apparatus.

An embodiment of the invention can also relate to a computer program product with a computer program which can be loaded directly into a memory of a control system with program segments for executing all the steps of the method for operating an X-ray apparatus and/or embodiments thereof when the program segments are executed by the control system. The invention can furthermore also relate to a computer-readable storage medium on which program segments that can be read and executed by a control system are stored in order to execute all the steps of an embodiment of the method for operating an X-ray apparatus and/or embodiments thereof when the program segments are executed by the control system.

An extensively software-based implementation has the advantage that it is also possible to retrofit control systems used to date in a simple way via a software update in order to work in the manner according to the invention. In addition to the computer program, such a computer program product can optionally comprise other additional parts, such as, for example, documentation and/or additional components, and hardware components, such as, for example hardware keys (dongles etc.) for using the software.

Generally, 'X-rays' refers to electromagnetic radiation with a wavelength between 10 nm and 1 pm, in particular between 5 pm and 100 pm, in particular between 8 pm and 50 pm. In particular, (in contrast to gamma radiation for example), X-rays are generated by high-energy electron processes, in particular by high-energy processes in the electron shells of atoms. In particular, X-ray tubes and particle accelerators are known for the generation of X-rays.

Monochromatic X-rays designates X-rays with a narrow intensity spectrum. In particular, X-rays are referred to a monochromatic X-rays with a wavelength $\lambda_0$ when the intensity spectrum is concentrated around the wavelength $\lambda_0$. In particular, X-rays are referred to as monochromatic X-rays when the proportion of the X-ray intensity in a wavelength interval around the wavelength $\lambda_0$ out of the entire X-ray intensity is greater than 50%, in particular greater than 75%, in particular greater than 90%. Herein, the width of the wavelength interval is in particular less than or equal to 40% of the wavelength $\lambda_0$, in particular less than or equal to 20% of the wavelength $\lambda_0$, in particular less than or equal to 10% of the wavelength $\lambda_0$, in particular less than or equal to 5% of the wavelength $\lambda_0$. If $I(\lambda)$ designates the intensity of the X-rays with wavelength $\lambda$ and $I_{int}$ ($\lambda_{max}$, $\lambda_{min}$) the integrated intensity between the wavelengths $\lambda_{min}$ and $\lambda_{max}$, the X-rays are monochromatic with wavelength $\lambda_0$ when $I_{int}$ ($\lambda_0-\Delta\lambda$, $\lambda_0+\Delta\lambda$)/$I_{int}$ ($\lambda_{max}$, $\lambda_{min}$)<a, wherein $\Delta\lambda=b\lambda_0$, in particular where a=0.5, in particular where a=0.75, in particular where a=0.9, and in particular where b=0.2, in particular where b=0.1, in particular where b=0.05.

Generally, a monochromator is an optical device for the spectral isolation of a specific wavelength from an incident quantity of incident electromagnetic radiation. A crystal monochromator is in particular a monochromator for X-rays, furthermore a crystal monochromator in particular includes a crystal. In the case of a crystal monochromator, spectral isolation is in particular achieved in that the X-rays are reflected at different lattice planes of the crystal resulting in path differences. Only when the wavelength of incident X-rays satisfies the Bragg condition does constructive interference occur, otherwise destructive interference occurs. As a result, the wavelength that satisfies the Bragg condition is spectrally isolated.

A multi-layer mirror includes at least two different materials which have different refractive indices for X-rays at a specific wavelength (optically dense material and optically thin material). Herein, the materials are arranged in layers with multiple alternations. The layer thicknesses are matched to one another such that, for the intended angle of incidence, the path difference corresponds to the wavelength (or a multiple of the wavelength) or one of the wavelengths (or a multiple of one of the wavelengths). This then results in constructive interference with reflection at the optically denser layers. Methods for the production of such multi-layer mirrors, in particular also curved multi-layer mirrors, are known for example from the U.S. Pat. No. 5,672,211A, the entire contents of which are hereby incorporated herein by reference.

A coated mirror, in particular a metal-coated mirror, can reflect X-rays in particular in the case of flat angles of incidence (measured between incident X-rays and the reflection surface) since the reflectivity of surfaces decreases as the angles of incidence become flatter. In particular, in the case of suitable refractive indices, the resulting total reflection can be used for the reflection of X-rays.

FIG. 1 shows a first example embodiment of an X-ray apparatus 100. The X-ray apparatus 100 includes an X-ray source 1, an X-ray detector 2 and an X-ray reflector 3.1. In this example embodiment, the X-ray apparatus 100 furthermore includes a patient support apparatus 5 on which a patient 6 or any examination object can be arranged.

The X-ray apparatus 100 is located in a space spanned by a first coordinate axis x, a second coordinate axis y and a third coordinate axis z. The three coordinate axes x, y, z form a Cartesian coordinate system.

In the example embodiment depicted, the X-ray source 1 includes an X-ray tube and advantageously a monochromator and a collimator. On the one hand, the X-ray spectrum emitted by the X-ray tube comprises portions caused by bremsstrahlung X-rays that occur due to deceleration of the electrons in the cathode material of the X-ray tube and have a wide energy distribution and, on the other hand, the X-ray spectrum has characteristic lines formed by the excitation and subsequent relaxation of electrons in the inner shells of atoms. The wide X-ray spectrum emitted can be filtered by Bragg reflection on the monochromator. This is done using a known crystal with known lattice constants and furthermore the incidence and exit angles of the X-rays in the X-ray source 1 are selected such that a Bragg reflex for the desired wavelength of the monochromatic X-rays is obtained. The collimator can be used in the beam path of the X-rays in the X-ray source 1 before or after the monochromator in order to convert fan-shaped X-rays into parallel X-rays. The collimator used can in particular be a parallel-hole collimator.

Alternatively, it is also possible for the X-ray source 1 not to comprise a monochromator, i.e. in this case, the X-ray source 1 is embodied to emit non-monochromatic X-rays or polychromatic X-rays.

Alternatively to an X-ray tube, the X-ray source 1 used can also be a particle accelerator, in particular for the acceleration of electrons on curved paths. Herein, X-rays can in particular occur as synchrotron radiation. Known in particular for the generation of monochromatic X-rays via particle accelerators are undulators, wherein an undulator consists of a periodic arrangement of strong magnets.

In the example embodiment depicted, the X-ray source 1 is embodied to emits X-rays 4 in a first direction 21. In other words, the X-rays 4 are propagated between the X-ray source 1 and the X-ray reflector 3.1 along the first direction 21. In the example embodiment depicted, the X-rays 4 are in particular parallel X-rays.

In the example embodiment depicted, the X-ray reflector 3.1 is embodied to reflect incident X-rays 4 with respect to a first direction 21 such that the reflected X-rays 4' are propagated along a second direction 22. To this end, the X-ray reflector 3.1 includes a multi-layer mirror with a layer thickness matched to the wavelength of the monochromatic X-rays 4. The exact structure of an X-ray reflector 3.1 with multi-layer mirror is explained in FIG. 7. In this example embodiment, the multi-layer mirror is arranged on a side 7 of the X-ray reflector 3.1, wherein the side 7 of the X-ray reflector 3.1 is flat. As a result, parallel incident X-rays 4 are reflected by the X-ray reflector 3.1 as parallel exiting X-rays 4'.

The side 7 of the X-ray reflector 3.1 is orthogonal to a third direction 23, wherein the third direction 23 is the bisector of the negative first direction 21 and the second direction 22. If the first direction 21 is defined by a vector v1 and the second direction 22 by a vector v2, the third direction 23 can in particular be defined by the vector $$v_3 = -\frac{v_1}{\|v_1\|} + \frac{v_2}{\|v_2\|}.$$

Herein, $\|v\|$ designates the norm or the length or the value of a vector. In other words, the third direction 23 is the normal of the side 7 of the X-ray reflector 3.1.

In the example embodiment depicted, the X-ray detector 2 is a flat-panel detector. The flat-panel detector includes in particular a scintillator, wherein the scintillator is embodied to convert X-rays into light in the visible spectrum. The light in the visible spectrum is converted into an electronic charge via a photodiode, which can, for example, be stored in a capacitor and/or with a transistor (in particular a "thin-film transistor", "TFT" for short). In this case, the capacitor and/or the transistor form readout electronics. Herein, in particular a plurality of scintillators and photodiodes and the associated readout electronics can be arranged in pixels. Alternatively, instead of a scintillator, it is also possible to use materials that convert the X-rays into an electric charge directly (photoconductor, for example amorphous selenium). The readout electronics can in particular also be arranged in an integrated circuit.

In the example embodiment depicted, the X-ray detector 2 is arranged orthogonally to the second direction 22. If the plurality of pixels of the X-ray detector 2 are arranged along a first pixel direction and a second pixel direction, wherein the second pixel direction differs from the first pixel direction, the X-ray detector 2 is in particular arranged orthogonally to the second direction 22 when the first pixel direction and the second pixel direction are in each case orthogonal to the second direction 22.

In the example embodiment depicted, a patient support apparatus 5 is arranged in the beam path between the X-ray reflector 3.1 and the X-ray detector 2. A patient support apparatus 5 can in particular be a patient bench. The patient support apparatus 5 can in particular be embodied movably with respect to each of the three coordinate axes x, y, z. During the movement of the patient support apparatus 5 with respect to each of the three coordinate axes x, y, z, in particular the orientation of the patient support apparatus 5 with respect to the three coordinate axes x, y, z can remain constant. The patient support apparatus 5 is in particular embodied to support a patient 6. The patient support apparatus 5 is in particular embodied as planar, furthermore the patient support apparatus 5 is substantially parallel to the plane spanned by the first coordinate axis x and the third coordinate axis z.

Figure 2:
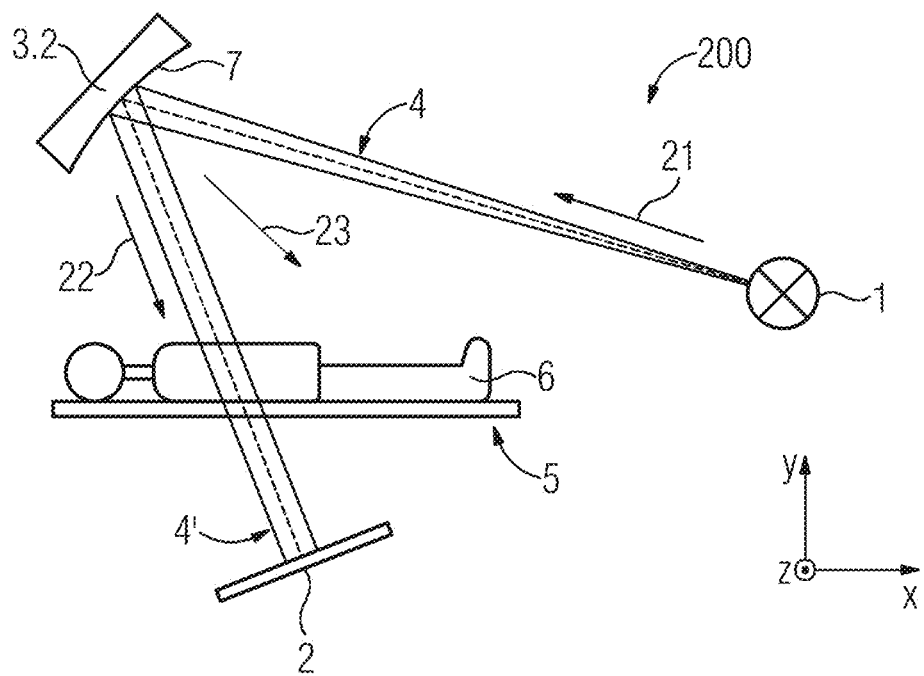
FIG. 2 a second example embodiment of an X-ray apparatus.
Figure 3:
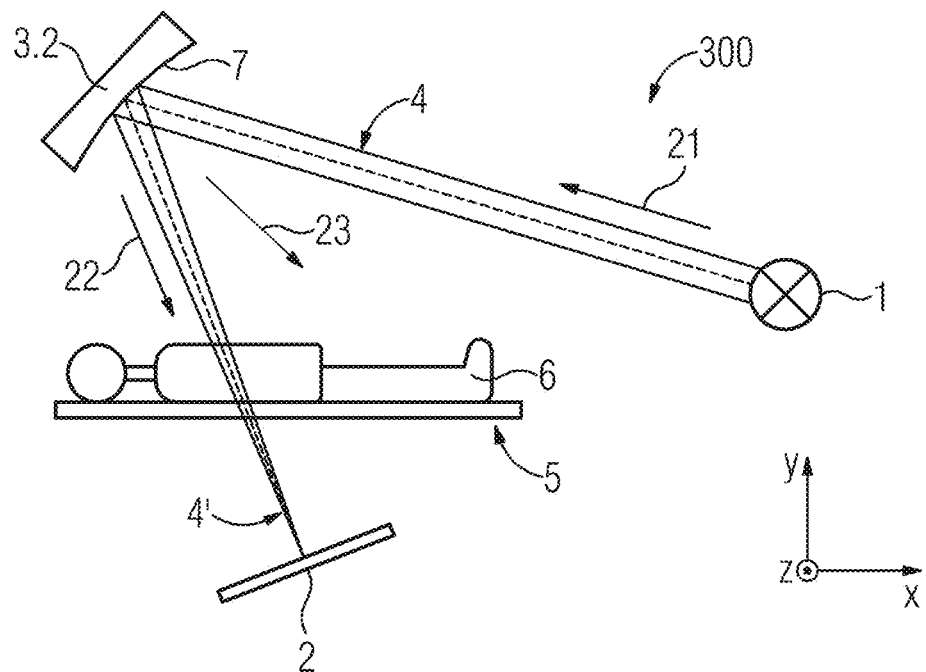
FIG. 3 a third example embodiment of an X-ray apparatus.

FIG. 2 and FIG. 3 show a second and a third example embodiment of an X-ray apparatus 200, 300. Herein, the X-ray apparatus 200, 300 includes an X-ray source 1, an X-ray detector 2 and an X-ray reflection facility 3.2, and a patient support apparatus 5. The X-ray source 1, the X-ray detector 2, the X-ray reflection facility 3.2 and the patient support apparatus 5 can all have advantageous embodiments and developments, which were described in respect of the corresponding components for the first example embodiment.

In contrast to the first example embodiment, in the second example embodiment in FIG. 2, the X-ray source 1 is embodied to generate cone-shaped X-rays 4, wherein the cone-shaped X-rays 4 are propagated between the X-ray source 1 and the X-ray reflection facility 3.2 along a first direction 21. As an approximation, here, the X-ray source 1 can be understood to be a point-like X-ray source 1, wherein the X-ray source 1 is then the apex of the cone-shaped X-rays 4. Herein, the X-ray reflection facility 3.2 is furthermore embodied to focus the X-rays 4. In particular, the X-ray reflection facility 3.2 is embodied to reflect coneshaped X-rays 4 as parallel X-rays 4'. The X-ray reflection facility 3.2 is in particular embodied to focus the X-rays 4 in that it comprises a concave side 7.

In the third example embodiment, the X-ray reflection facility 3.2 is also embodied to focus the X-rays 4. In particular, the X-ray reflection facility 3.2 is embodied to reflect parallel X-rays 4 as cone-shaped X-rays 4', in particular in that they comprise a concave side 7.

Figure 4:
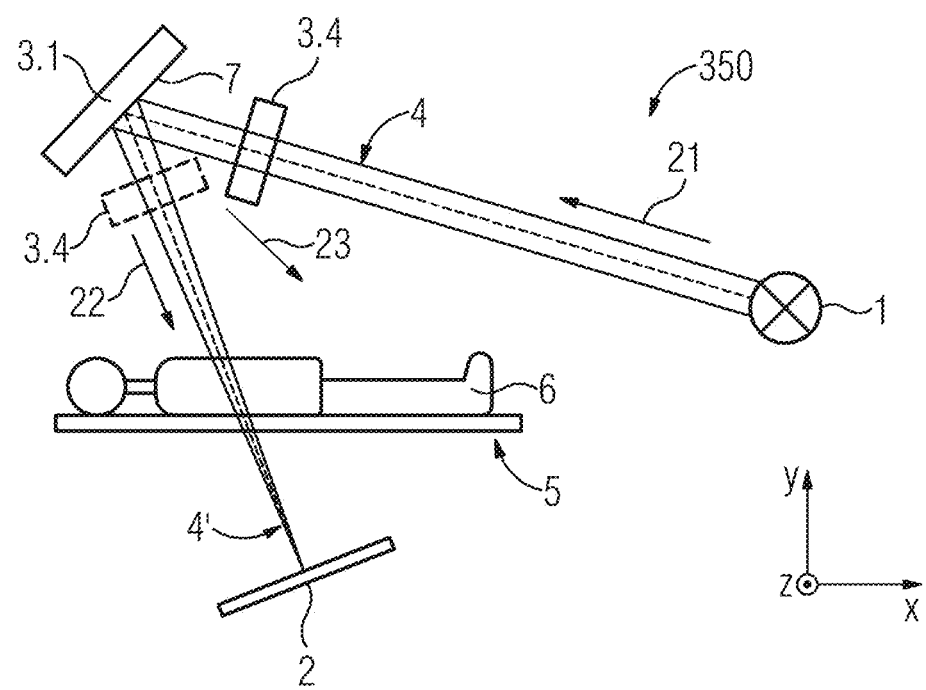
FIG. 4 a fourth example embodiment of an X-ray apparatus.

FIG. 4 shows a fourth example embodiment of an X-ray apparatus 350. In this example embodiment, the X-ray apparatus also includes an X-ray source 1, an X-ray detector 2 and an X-ray reflector 3.1. FIG. 4 furthermore depicts a patient support apparatus 5 on which a patient 5 can be supported. The X-ray source 1, the X-ray detector 2, the X-ray reflection facility 3.1 and the patient support apparatus 5 can all have advantageous embodiments and developments, which were described in respect of the corresponding components for the first example embodiment.

In this fourth example embodiment, the X-ray apparatus 350 furthermore includes a Fresnel zone plate 3.4, alternatively to the Fresnel zone plate 3.4, it is also possible to use a refractive X-ray lens. In this example embodiment, the Fresnel zone plate 3.4 is arranged between the X-ray source 1 and the X-ray reflector 3.1. Alternatively, as indicated by dashed lines in FIG. 4, the Fresnel zone plate 3.4 can be arranged in the beam path between the X-ray reflector 3.1 and the X-ray detector 2.

In this fourth example embodiment, the X-ray reflector 3.1 is not embodied to focus X-rays, and the X-rays are solely focused by the Fresnel zone plate 3.4. Alternatively, the X-ray reflector 3.1 can also be embodied to focus X-rays, in this case, the X-ray reflector 3.1 and the Fresnel zone plate 3.4 then interact to focus the X-rays.

Figure 5:
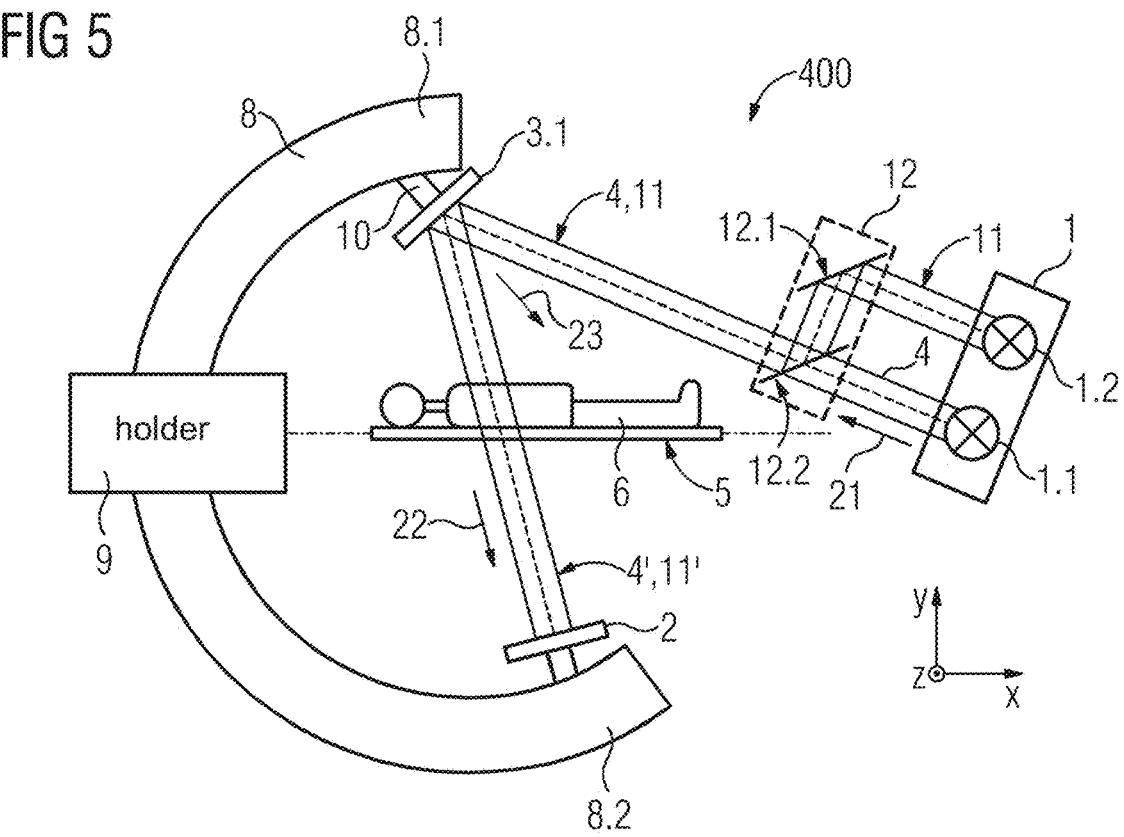
FIG. 5 a fifth example embodiment of an X-ray apparatus.
Figure 6:
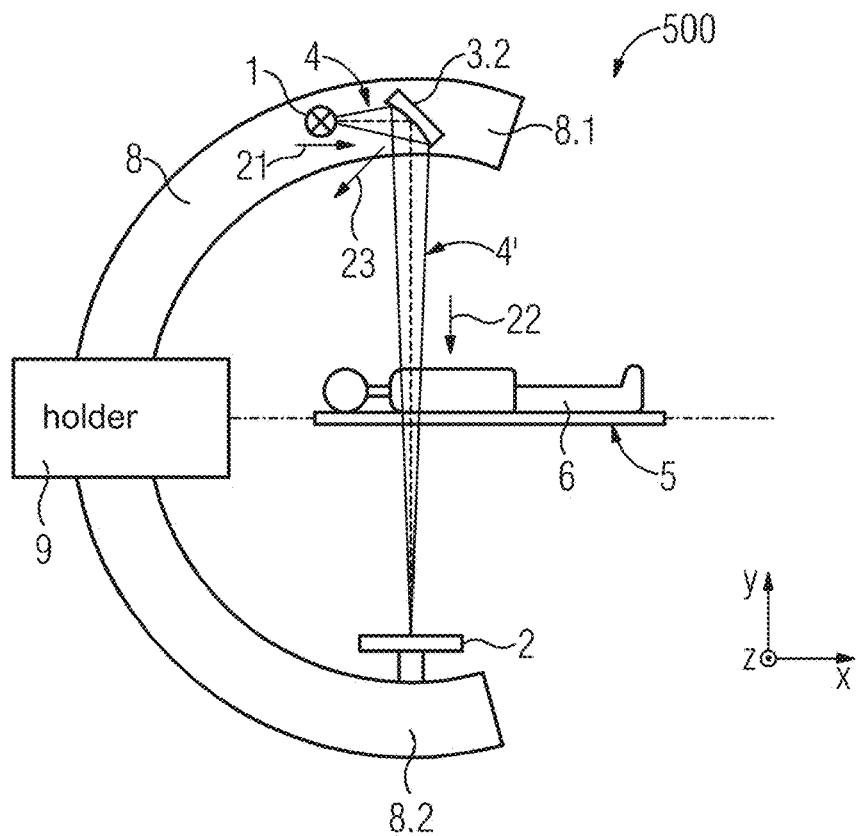
FIG. 6 a sixth example embodiment of an X-ray apparatus.

FIG. 5 and FIG. 6 show a fifth and a sixth example embodiment of an X-ray apparatus 400, 500. In this example embodiment, the X-ray apparatus also includes an X-ray source 1, an X-ray detector 2 and an X-ray reflector 3.1, 3.2. Furthermore, FIG. 5 and FIG. 6 depict a patient support apparatus 5 on which a patient 6 can be supported. The X-ray source 1, the X-ray detector 2, the X-ray reflection facility 3.1, 3.2 and the patient support apparatus 5 can all have advantageous embodiments and developments, which were described in respect of the corresponding components for the first example embodiment.

In the fifth example embodiment, both the X-ray reflector 3.1 and the X-ray detector 2 are arranged on a C-arm 8. The X-ray reflector 3.1 is in particular arranged on a first end 8.1 of the C-arm 8 and the X-ray detector 2 is arranged on a second end 8.2 of the C-arm. Herein, the first end 8.1 and the second end 8.2 of the C-arm are located on opposite sides of the patient 6 or the patient support apparatus 5 during the recording of X-ray images. In the sixth example embodiment, the X-ray source 1, the X-ray detector 2 and the X-ray reflector 3.2 are arranged on a C-arm. In particular, the X-ray source 1 and the X-ray reflector 3.2 are arranged on a first end 8.1 of the C-arm and the X-ray detector is arranged on a second end 8.2 of the C-arm 8. In particular in the case of stationary C-arms, the X-ray detector 2 can be shifted in or against the second direction y.

Herein, the C-arm 8 is arranged on a holder 9. The holder enables the C-arm 8 to be rotated about different axes of rotation. Alternatively to the holder 9, the arm can also be arranged on a 6-axis articulated robot. For example, the C-arm can be rotated about an axis of rotation parallel to the third coordinate axis z. Furthermore, the C-arm can be rotated about a further axis of rotation parallel to a plane spanned by the first coordinate axis x and the second coordinate axis y. Hence, the X-ray detector 2 and the X-ray reflector 3.1, 3.2 can also be rotated simultaneously about the respective axis of rotation. Furthermore, in the sixth example embodiment, the X-ray source 1, the X-ray detector 2 and the X-ray reflector 3.1, 3.2 can be rotated simultaneously about the respective axis of rotation. The spatial position of the holder 9 can be shifted, for example the holder 9 can in turn be arranged on a movable arm with a plurality of axes of motion or the holder 9 can be embodied as mobile.

Alternatively, both the X-ray reflector 3.1 and the X-ray detector 2 can be arranged on another common structure, wherein the other common structure can in particular be embodied as rotatable. The other common structure can in particular be a gantry of a computed tomography scanner.

In the fifth example embodiment, the X-ray source 1 is furthermore embodied to emit light in the visible spectrum 11. To this end, the X-ray source 1 includes an actual X-ray source 1.1 embodied to generate X-rays 4 and one or more light sources 1.2, embodied to generate light in the optically visible spectrum 11. Herein, the actual X-ray source 1.1 in particular includes an X-ray tube and the one or more light sources 1.2 can in particular be one or more lasers.

Herein, the light in the visible spectrum 11 is preferably also emitted by the light source 1.2 along the first direction but offset in parallel to the X-rays 4. A deflection system 12 enables the light in the optical spectrum 11 to be brought into coincidence with the X-rays 4. In the fifth example embodiment 12 depicted, the deflection system 12 includes two mirrors 12.1, 12.2 embodied to reflect light in the optical spectrum. The mirror 12.2 in the beam path of the X-rays 4 is transparent to X-rays. The deflection system 12 can also be part of the X-ray source 1. In the example embodiment depicted, the light source 1.2 also emits light in the optical visible spectrum 11 when the actual X-ray source is not generating X-rays 4. Alternatively, it is also possible for the light source 1.2 and the actual X-ray source 1.1 to be synchronized, i.e. the light source 1.2 substantially only emits light in the optically visible spectrum 11 when the actual X-ray source 1.1 generates X-rays 4.

In this example embodiment, the X-ray reflector 3.1 is embodied to emit light in the optically visible spectrum 11 similarly to or in the same way as X-rays 4. In particular, the light in the optically visible spectrum 11, which is propagated along the first direction 21, is reflected by the X-ray reflector 3.2 in the second direction 22.

Figure 7:
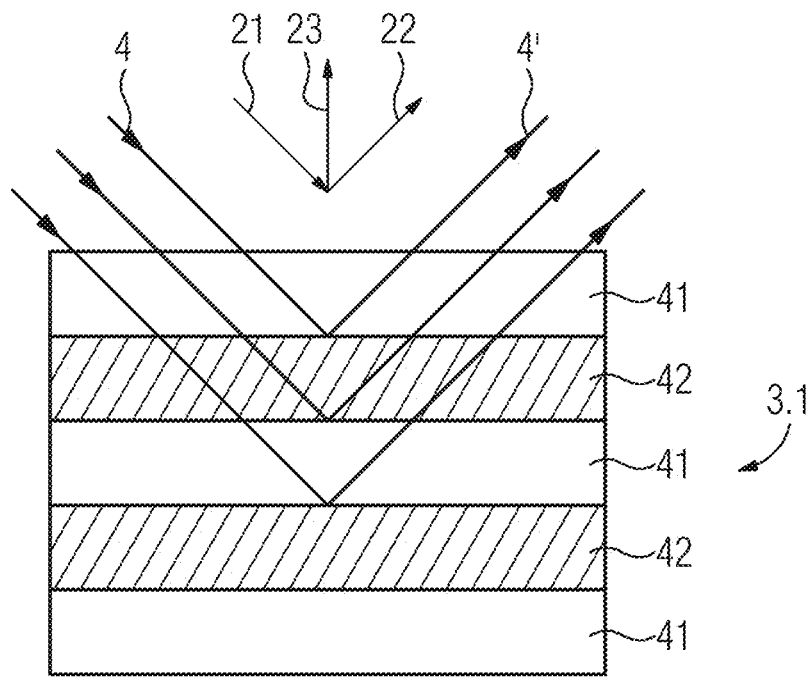
FIG. 7 an X-ray reflector including a multi-layer mirror.

FIG. 7 shows an X-ray reflector 3.1 including a multi-layer mirror. The multi-layer mirror reflects incident X-rays 4 along a first direction 21 (depicted by the vector $v_1$) in exiting X-rays 4' along a second direction 22 (depicted by the vector $v_2$). In particular, the multi-layer mirror is embodied planar with respect to a first and a second extension direction, wherein the first and the second extension direction are different and wherein the first and the second extension direction are in each case orthogonal to a third direction 23 (depicted by the vector $v_3$). The third direction 23 is in particular the bisector of the negative first direction 21 and the second direction 22.

The multi-layer mirror consists of a multiplicity of layers 41, 42, wherein the layers have a planar extension flat with respect to the first and the second extension direction. The layers 41, 42 consist of two different materials with different optical activity, in particular with different refractive indices for electromagnetic waves. In particular, a first layer 41 and a second layer 42 alternate in each case. The extension of the first layers 41 and the second layers 42 with respect to the third direction 23 is designated the layer thickness d.

If $\lambda$ designates the wavelength of the incident X-rays 4 and $\varphi$ the angle between the third direction 23 and the negative first direction 21 or the angle between the third direction 23 and the second direction 22, the incident X-rays are reflected when the condition $n \cdot \lambda = d \cdot \cos(\varphi)$ is satisfied (wherein $n \geq 1$ is a natural number). In particular, $\cos(\varphi) = v_1 \cdot v_2 / |v_1| \cdot |v_2|$ applies, wherein $v_1 \cdot v_2$ designates the scalar product of the vectors $v_1$ and $v_2$.

For example, in the example embodiment depicted, a wavelength of $\lambda = 13.5$ nm can be selected and the first layers 41 can consist of silicon (optically thin medium) and the second layers 42 of molybdenum (optically dense medium).

In the case of a multi-layer mirror, the layers 41, 42 can in particular be applied to a substrate (for example silicon). The layers 41, 42 can in particular be vapor-deposited onto the substrate, alternatively, it is also possible to use photolithographic methods.

Figure 8:
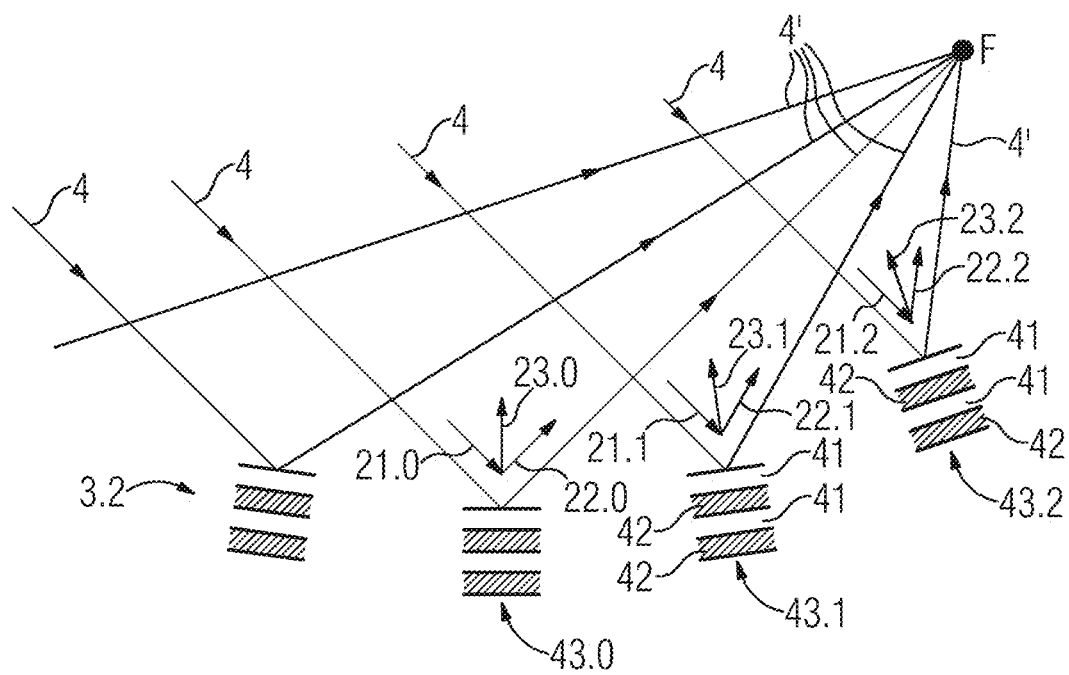
FIG. 8 an X-ray reflector including a curved multi-layer mirror.

FIG. 8 shows a X-ray reflector 3.2 including a multi-layer mirror embodied to focus X-rays 4, 4'. Herein, FIG. 8 depicts a plurality of segments 43.0, 43.1, 43.2 of the multi-layer mirror depicted. The segment 43.0 can in particular be located in the center or in a radial center of symmetry of the multi-layer mirror. The sections of the multi-layer mirror outside the segments 43.0, 43.1, 43.2 are not depicted. In particular, the multi-layer mirror depicted can be understood to be curved or concave.

The multi-layer mirror can in particular consist of a multiplicity of planar segments 43.0, 43.1, 43.2, wherein the segments 43.0, 43.1, 43.2 have substantially no curvature. In other words, the multi-layer mirror is structured in a facet-like manner from the individual segments 43.0, 43.1, 43.2. Herein, the individual segments can share a point or a line segment with adjacent segments. Alternatively, the planar segments 43.0, 43.1, 43.2 can also be concave. Alternatively, the multi-layer mirror can also be embodied as curved, in particular continuously curved, in particular as concave. In this case, the segments 43.0, 43.1, 43.2 can be assumed to be infinitesimally small. The properties of the segments 43.0, 43.1, 43.2 (in particular the orientation of the segments 43.0, 43.1, 43.2 and the layer thickness of the respective segments) in both cases can in particular only depend on the distance of the respective segment 43.0, 43.1, 43.2 from the radial center of symmetry of the multi-layer mirror.

In the case of a multi-layer mirror, the layers 41, 42 or the segments 43.0, 43.1, 43.2 can in particular be applied to a substrate (for example silicon). The layers 41, 42 or the segments 43.0, 43.1, 43.2 can in particular be vapor-deposited onto the substrate, alternatively, it is also possible to use photolithographic methods, in particular to generate the segments or the continuous curvature.

In the example embodiment depicted, the X-rays are propagated 4 between the X-ray source 1 and the X-ray reflector 3.2 as parallel X-rays along a first direction 21. Furthermore, the X-rays are propagated 4' between the X-ray reflector 3.2 and the X-ray detector 2 as cone-shaped X-rays along a second direction 22. Herein, the X-rays are focused in a focal point F. Alternatively, the X-rays 4 between the X-ray source 1 and the X-ray reflector 3.2 could also be propagated as concave X-rays along the first direction 21 and furthermore the X-rays 4' between the X-ray reflector 3.2 and the X-ray detector 2 could be propagated as cone-shaped X-rays along the second direction 22. As another alternative, the X-rays 4 between the X-ray source 1 and the X-ray reflector 3.2 could also be propagated as concave X-rays along the first direction 21 and furthermore the X-rays between the X-ray reflector 3.2 and the X-ray detector 2 could be propagated as cone-shaped X-rays along the second direction 22.

The X-rays are incident on all the segments 43.0, 43.1, 43.2 with respect to the first direction 21, in particular therefore the segment-specific incidence direction 21.0, 21.1, 21.2 for all the segments 43.0, 43.1, 43.2 is identical to the first direction 21. To achieve focusing, however, the segment-specific exit direction 22.0, 22.1, 22.2 deviates from the second direction 22 (apart from in the segment 43.0 in the center of symmetry). Accordingly, the segment-specific perpendicular line 23.0, 23.1, 23.2 deviates from the third direction.

In particular, therefore, the angle between the negative incidence direction 21.0, 21.1, 21.2 and the segment-specific perpendicular line 23.0, 23.1, 23.2 or the angle between the exit direction 22.0, 22.1, 22.2 is segment-specific. If $\varphi_i$ designates this angle in the i-th segment 43.0, 43.1, 43.2, the layer thickness $d_i$ of the i-th segment 43.0, 43.1, 43.2 must satisfy the Bragg condition $n\lambda=2d_i\cdot\cos(\varphi_i)$, in particular, therefore, the layer thickness $d_i$ of the i-th segment 43.0, 43.1, 43.2 is dependent upon the respective angle of reflection $\varphi_i$.

The segments 43.0, 43.1, 43.2 can in particular also be infinitesimal segments 43.0, 43.1, 43.2. In this case, the angle of reflection $\varphi(r)$ of an infinitesimal segment 43.0, 43.1, 43.2 is a function of the distance r of this infinitesimal segment 43.0, 43.1, 43.2 from the center of symmetry and in particular the layer thickness d(r) of this infinitesimal segment 43.0, 43.1, 43.2 is also a function of the distance r of the infinitesimal segment 43.0, 43.1, 43.2 from the center of symmetry, wherein the Bragg condition $n\lambda=2d(r)\cdot\cos(\varphi(r))$ must again be satisfied for each radius r. Methods for producing such curved multi-layer mirrors, are for example known from the U.S. Pat. No. 5,672,211A.

Figure 9:
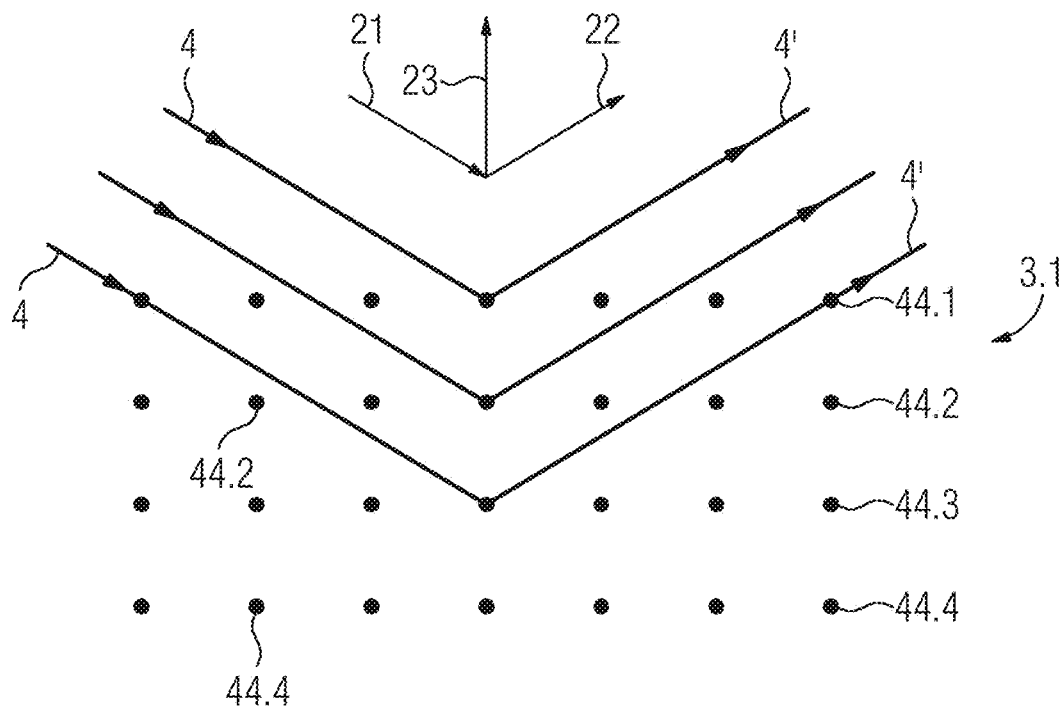
FIG. 9 an X-ray reflector including a crystal monochromator.

FIG. 9 shows an X-ray reflector 3.1 including a crystal monochromator. The crystal monochromator reflects incident X-rays 4 along a first direction 21 (corresponding to the vector $v_1$) as exiting X-rays 4' along a second direction 22 (corresponding to the vector $v_2$). In particular, the crystal monochromator is embodied as planar with respect to a first and a second extension direction, wherein the first and the second extension direction are different and wherein the first and the second extension direction are in each case orthogonal to a third direction 23 (depicted by the vector $v_3$). The third direction 23 is in particular the bisector of the negative first direction 21 and the second direction 22.

The crystal monochromator includes a multiplicity of atoms 44.1, 44.2, 44.3, 44.4 arranged in a crystal lattice. Herein, the atoms are arranged in orthogonal layers with respect to the third direction, for example a first layer includes atoms 44.1, and a second layer includes atoms 44.2, a third layer includes atoms 44.3, and a fourth layer includes atoms 44.4. The layer distance of the layers is referred to as the layer thickness d. The layers can be any layers of the crystal monochromator that do not necessarily contain the basis vectors of the crystal lattice. If the basis vectors of the crystal lattice are $e_1$, $e_2$, $e_3$, in principle all the planes spanned by two linearly independent plane vectors can form layers, wherein each of the linearly independent plane vectors can be depicted as a linear combination $ae_1+be_2+ce_3$ of the basis vectors with integers a, b, c. In the case of non-primitive lattices (for example body-centered cubic lattices or face-centered cubic lattices), it is even possible to use specific linear combinations with non-integer a, b, c.

X-rays 4, 4' are generally able to penetrate the crystal; therefore; the X-rays are reflected not only at the crystal surface but at a plurality of lattice planes of the crystal lattice. Herein, X-rays 4, 4' reflected at outermost lattice plane cover a shorter distance than X-rays reflected by a lattice plane inside the crystal. This difference in distance is called the path difference. Depending on this path distance, constructive or destructive interference of the X-rays reflected at different lattice planes may occur.

If $\lambda$ designates the wavelength of the incident X-rays 4, and $\varphi$ the angle between the third direction 23 and the negative first direction 21 or the angle between the third direction 23 and the second direction 22, constructive interference results when the condition $n\cdot\lambda=d\cdot\cos(\varphi)$ is satisfied (wherein $n\geq 1$ is a natural number). In particular, $\cos(\varphi)=v_1\cdot v_2/|v_1|\cdot|v_2|$ applies, wherein $v_1\cdot v_2$ designates the scalar product of the vectors $v_1$ and $v_2$. In all other directions, destructive interference occurs so that the incident X-rays are only reflected when the condition $n\cdot\lambda=d\cdot\cos(\varphi)$ is satisfied.

The crystal used in the crystal monochromator can, for example, be a lithium fluoride crystal with d=0.201 nm. It is furthermore possible to use a sodium chloride crystal with d=0.27 nm. Alternatively, it is also possible to use a silicon-molybdenum crystal with d=13.5 nm. However, it is obviously also possible to use other crystals for a crystal monochromator.

Figure 10:
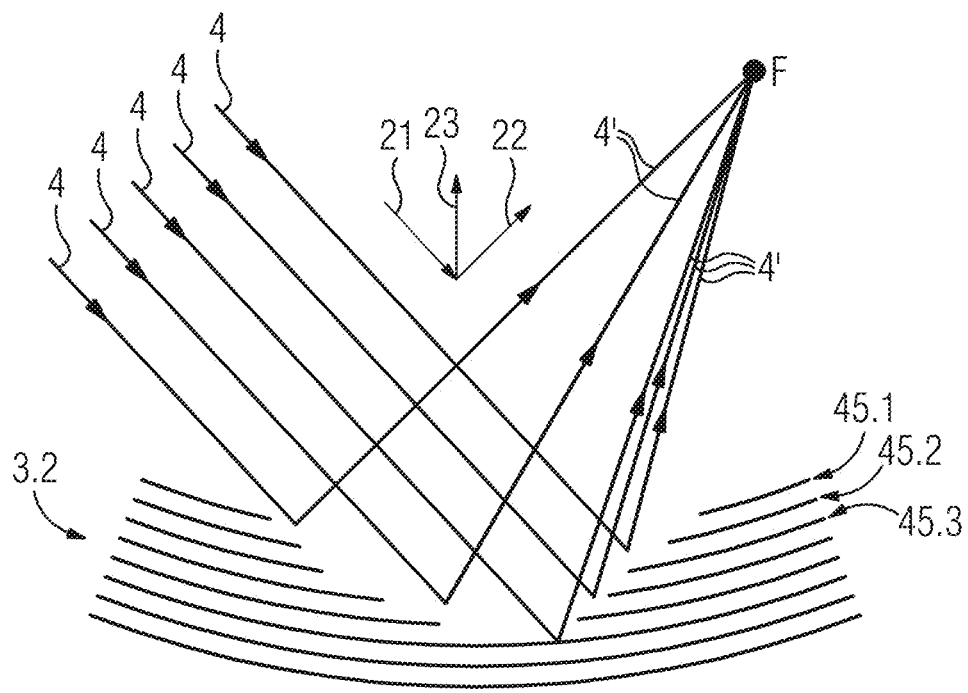
FIG. 10 an X-ray reflector including a curved crystal monochromator.

FIG. 10 shows an X-ray reflector 3.2 including a curved crystal monochromator (or a curved crystal) embodied to focus X-rays 4. Herein, parallel incident X-rays 4, wherein the incident X-rays are propagated with respect to a first direction 21, are reflected as cone-shaped X-rays 4' with the apex F, wherein these exiting X-rays are propagated with respect to a second direction 22. Herein, the crystal monochromator is embodied as rotationally symmetrical with respect to the third direction 23, wherein the third direction 23 is the bisector of the negative first direction 21 and the second direction 22.

Herein, the crystal monochromator is bent and, as a result, the crystal layers 45.1, 45.2, 45.3 of the crystal monochromator are also bent. Furthermore, a concave bulge has been milled out of the crystal monochromator. Alternatively, the concave bulge can also be generated by influencing the crystal monochromator growth process.

In the example embodiment depicted, the crystal monochromator is embodied as bent. However, alternatively, the crystal monochromator can also be embodied as flat, in particular in that the crystal layers 45.1, 45.2, 45.3 of the crystal monochromator are not bent. In this case, it is again possible for a concave bulge to be milled out of the crystal monochromator. Alternatively, in this case, the concave bulge can again be generated by influencing the crystal monochromator growth process.

Figure 11:
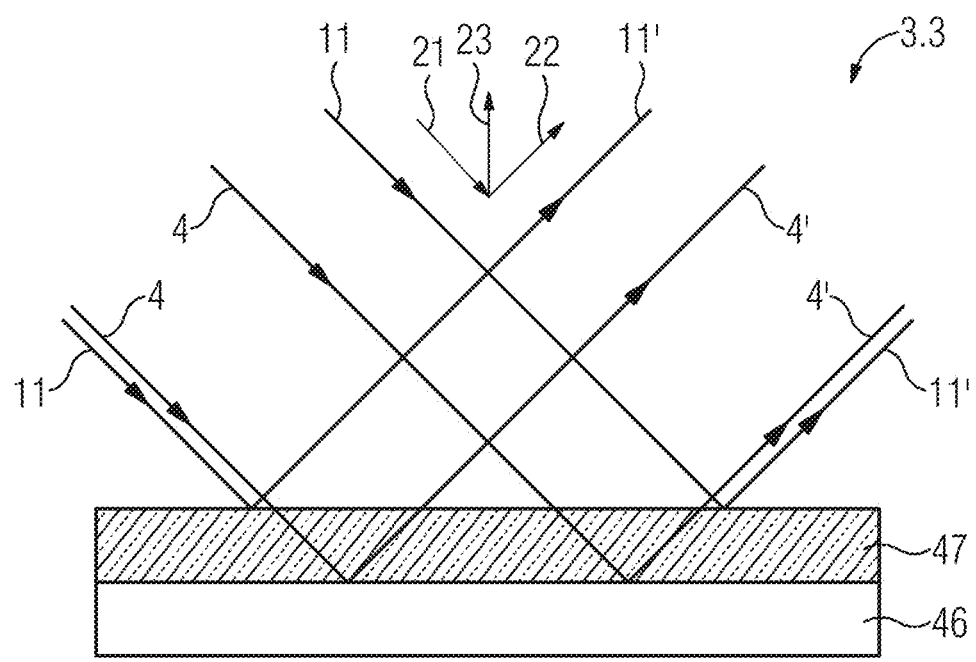
FIG. 11 an X-ray reflector embodied to reflect X-rays and light in the optically visible spectrum, FIG. 12 a sequence diagram of a method for operating an X-ray apparatus.

FIG. 11 shows an X-ray reflector 3.1, which is embodied to reflect X-rays 4 and to reflect light in the optically visible spectrum 11. In the example embodiment depicted, incident X-rays 4, which are propagated with respect to the first direction 21, are reflected as exiting X-rays 4', which are propagated with respect to a second direction 22. Furthermore, incident light in the optically visible spectrum 11, which is propagated with respect to a first direction 21, is reflected as exiting light in the optically visible spectrum 11', which is propagated with respect to the second direction 22.

The X-ray reflector 3.1 depicted includes a first reflection unit 46 and a second reflection unit 47, which are arranged one on top of the other with respect to the third direction 23. The first reflection unit 47 is embodied to reflect light in the optically visible spectrum 11, 11' and is furthermore transparent to X-rays 4, 4'. The first reflection unit 46 is embodied to reflect X-rays 4, 4'.

In the example embodiment depicted, the width and the position of the parallel incident light in the optically visible spectrum 11 are selected such that both the incident X-rays 4 and the exiting X-rays 4' always travel within the incident light in the optically visible spectrum 11 or the exiting light in the optically visible spectrum 11'. As a result, it is possible to ensure that the entire spatial radiation pattern of the X-rays 4, 4' is visualized by the light in the optically visible spectrum.

As an alternative to the first reflection unit 46 and second reflection unit 47 depicted arranged one on top of the other with respect to the third direction 23, it is also possible, for mirrors 12.1, 12.2 transparent to X-rays 4, 4' to be partially arranged in the beam path of the X-rays, as depicted in FIG. 5, for example. The mirrors 12.1, 12.2 can divert light in the optically visible spectrum 11 out of the beam path of the incident X-rays 4 onto the first reflection unit 46. Further mirrors 12.1, 12.2 can reflect the light reflected at the first reflection unit in the optical spectrum 11' back into the beam path of the reflected X-rays 4'. Herein, the first reflection unit can be freely positioned in space.

Figure 12:
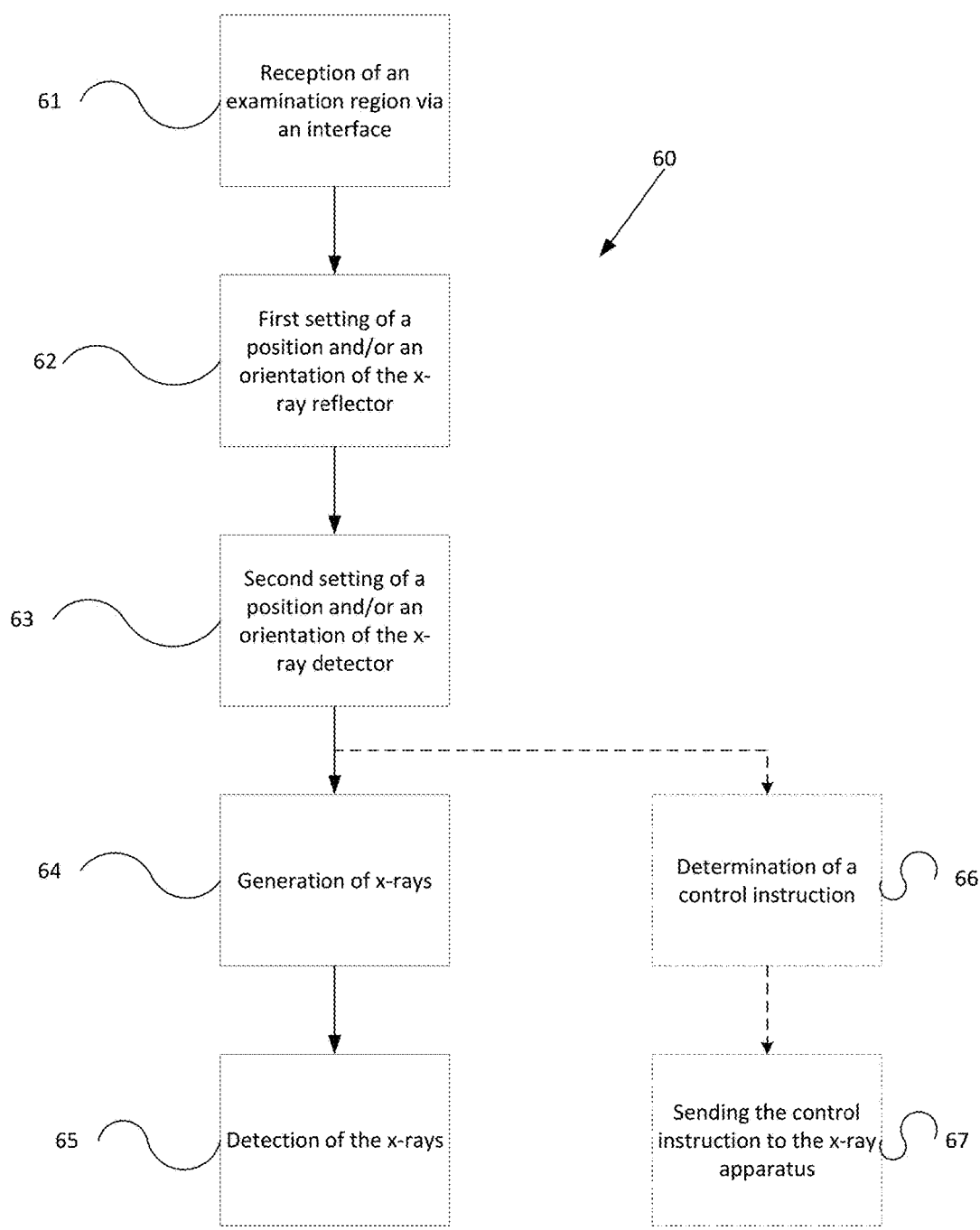

FIG. 12 shows a sequence diagram 60 of an example embodiment of the method for operating an X-ray apparatus 100, 200, 300, 350, 400, 500.

The first step of the example embodiment depicted is the reception 61 of an examination region via an interface. In the example embodiment depicted, the examination region is input by an operator by device-fixed coordinates relative to the X-ray apparatus 100, 200, 300, 350, 400, 500, alternatively it is also possible to use spatially fixed coordinates. Alternatively, the operator can also set the examination region by shifting rotatable axes of the X-ray apparatus 100, 200, 300, 350, 400, 500 and/or by shifting the X-ray apparatus 100, 200, 300, 350, 400, 500. In particular, the location of the examination region relative to specified parts of the X-ray apparatus 100, 200, 300, 350, 400, 500 is known to the operator and the control system. In particular, in this case, to receive REC of the examination region, coordinates of the X-ray apparatus 100, 200, 300, 350, 400, 500 (in particular also the position of movable axes) can be received and then converted into device-fixed and/or spatially fixed coordinates of the examination region.

The second step of the example embodiment depicted is the first setting 62 of a position and/or an orientation of the X-ray reflector 3.1, 3.2 so that the reflected X-rays (4') reflected by the X-ray reflector 3.1, 3.2 irradiate the examination region.

In the following, it is assumed that the X-ray reflector 3.1, 3.2 and the X-ray detector can be simultaneously rotated about a common first axis of rotation through the origin of the coordinates and parallel to the third coordinate axis z. Furthermore, it is assumed that the X-ray reflector 3.1, 3.2, the X-ray source 1 and the X-ray detector 2 are arranged in a plane spanned by the first coordinate axis x and the second coordinate axis y through the origin of the coordinates. In particular, the choice of the plane and the axis of rotation does not restrict generality.

The coordinates $x_Q$ of the X-ray source 1, $x_D$ of the X-ray detector 2 and $x_R$ of the X-ray reflector 3.1, 3.2 are then introduced as follows:

$$x_Q = \begin{pmatrix} q \\ 0 \end{pmatrix}; \quad x_D = \begin{pmatrix} 0 \\ -b \end{pmatrix}; \quad x_R = \begin{pmatrix} 0 \\ a \end{pmatrix}$$

Herein, q>0, b>0 and a>0 are real numbers. This enables the determination of vectors $v_1$ and $v_2$, which depict or determine the first direction 21 and the second direction 22:

$$v_1 = \begin{pmatrix} -q \\ a \end{pmatrix}; \quad v_2 = \begin{pmatrix} 0 \\ -a-b \end{pmatrix}$$

The third direction 23 can then be determined as the bisector of the negative first direction 21 and the second direction 22:

$$v_3 = \frac{1}{\sqrt{a^2+q^2}} \begin{pmatrix} q \\ -a \end{pmatrix} + \frac{1}{\sqrt{(a+b)^2}} \begin{pmatrix} 0 \\ -a-b \end{pmatrix} = \frac{1}{\sqrt{a^2+q^2}} \begin{pmatrix} q \\ -a \end{pmatrix} + \begin{pmatrix} 0 \\ -1 \end{pmatrix}$$

On the first setting 62, it is then in particular possible for the orientation of the X-ray reflector 3.1, 3.2 to be set such that the X-ray reflector is arranged orthogonally to the third direction 23. The third direction is in particular independent of the distance b of the X-ray detector 2 from the origin of the coordinates.

If the X-ray source 1 is arranged not at the coordinates (q, 0), but at the coordinates ($q_1$, $q_2$), the following relationships are obtained for the first direction 21 and the second direction 22:

$$v_1 = \begin{pmatrix} -q_1 \\ a-q_2 \end{pmatrix}; \quad v_2 = \begin{pmatrix} 0 \\ -a-b \end{pmatrix}$$

Furthermore, hence, the following is obtained for the third direction 23:

$$v_3 = \frac{1}{\sqrt{(a-q_2)^2 + q_1^2}} \begin{pmatrix} q_1 \\ q_2-a \end{pmatrix} + \begin{pmatrix} 0 \\ -1 \end{pmatrix}$$

If the X-ray detector 2 and the X-ray reflector 3.1, 3.2 are rotated with an angle α about the common first axis of rotation, the coordinates $x_D$ and $x_R$ are obtained as:

$$x_D = \begin{pmatrix} b \cdot \sin(\alpha) \\ -b \cdot \cos(\alpha) \end{pmatrix}; \quad x_R = \begin{pmatrix} -a \cdot \sin(\alpha) \\ a \cdot \cos(\alpha) \end{pmatrix}$$

This results in the following for the first direction 21 and for the second direction 22:

$$v_1 = \begin{pmatrix} -a \cdot \sin(\alpha) - q_1 \\ a \cdot \cos(\alpha) - q_2 \end{pmatrix}; \quad v_2 = \begin{pmatrix} (a+b) \cdot \sin(\alpha) \\ -(a+b) \cdot \cos(\alpha) \end{pmatrix}$$

Furthermore, hence, the following is obtained for the third direction 23:

$$v_3 = \frac{1}{\sqrt{a^2 + 2a(q_1\sin(\alpha) - q_2\cos(\alpha)) + q_1^2 + q_2^2}} \begin{pmatrix} -a \cdot \sin(\alpha) - q_1 \\ a \cdot \cos(\alpha) - q_2 \end{pmatrix} + \begin{pmatrix} \sin(\alpha) \\ -\cos(\alpha) \end{pmatrix}$$

A further optional step of the example embodiment depicted is the second setting 63 of a position and/or an orientation of the X-ray detector 2 so that the X-ray detector 2 is arranged orthogonally to the X-rays 4' reflected by the X-ray reflector 3.1, 3.2. In this example embodiment, the orientation of the X-ray detector is set such that the X-ray detector is arranged orthogonally to the second direction 22, wherein the second direction 22 is defined by the calculated vector v2.

In particular, alternatively it is also possible for the coordinates $x_R$ of the X-ray source 1 to be determined with specified coordinates $x_D$ of the X-ray detector 2 and $x_R$ of the X-ray reflector 3.1, 3.2 and a specified angle of reflection p (between the negative first direction 21 and the third direction 23 or between the second direction 22 and the third direction 23). If the specified coordinates used are $$x_D = \begin{pmatrix} 0 \\ -b \end{pmatrix}; \quad x_R = \begin{pmatrix} 0 \\ a \end{pmatrix}$$

the following unit vectors are obtained for the third direction 23 and the first direction 21

$$v_3 = \begin{pmatrix} \sin(\varphi) \\ -\cos(\varphi) \end{pmatrix}; \quad v_1 = \begin{pmatrix} -\sin(2\varphi) \\ \cos(2\varphi) \end{pmatrix}.$$

Therefore, the coordinates $x_R$ of the X-ray source 1 have to be selected as $$x_R = \begin{pmatrix} \sin(2\varphi) \\ a - r \cdot \cos(2\varphi) \end{pmatrix}.$$

Herein, r designates a freely selectable distance between the X-ray source 1 and the X-ray reflector 3.1, 3.2. Equivalently, coordinate transformation can also enable the position of the X-ray source 1 to be deemed to be known and the position of the X-ray reflector 3.1, 3.2 and/or the X-ray detector 2 determined. Herein, the orientation of the X-ray reflector 3.1, 3.2 is in each case clearly defined by the third direction 23.

The next two steps of the method depicted are the generation 64 of X-rays 4 via the X-ray source 1 and the detection 65 of the X-rays 4' via the X-ray detector 2. These two steps can be replaced by the determination 66 of a control instruction by way of the computing unit, wherein the X-ray apparatus 100, 200, 300, 350, 400, 500 triggers the recording of X-ray images based on the control instruction and by sending 67 the control instruction to the X-ray apparatus 100, 200, 300, 350, 400, 500 via the interface.

Where not explicitly mentioned, but advisable and in accordance with the sense of the invention, individual example embodiments, individual partial aspects or features thereof can be combined with one another or exchanged without the leaving the scope of the present invention. Where transferrable, advantages of the invention described with reference to one example embodiment also apply to other example embodiments without this being explicitly mentioned. In particular, the features of the example embodiment depicted in FIG. 1 to FIG. 4 can also be implemented in the example embodiments depicted in FIG. 5 and FIG. 6. In particular, the X-ray apparatuses 100, 200, 300, 350, 400, 500 depicted in FIG. 1 to FIG. 6 can comprise a X-ray reflector 3.1, 3.2 according to that depicted in FIGS. 7 to 11.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray apparatus, comprising:
   an X-ray source embodied to generate X-rays;
   an X-ray detector; and
   an X-ray-reflector, embodied to reflect the X-rays generated by the X-ray source such that reflected X-rays hit the X-ray detector, wherein
   the X-ray reflector and the X-ray detector are rotatable simultaneously about at least one of a common first axis of rotation and
   a common second axis of rotation.

2. The X-ray apparatus of claim 1, wherein the X-rays generated by the X-ray source are propagated between the X-ray source and the X-ray-reflector along a first direction, and wherein the X-rays are propagated between the X-ray-reflector and the X-ray detector along a second direction, the first direction being different from the second direction.

3. The X-ray apparatus of claim 2, wherein the X-ray detector is arranged orthogonally to the second direction.

4. The X-ray apparatus of claim 3, wherein the X-ray reflector is arranged orthogonally to a third direction, wherein the third direction is a bisector of a negative first direction and the second direction.

5. The X-ray apparatus of claim 2, wherein the X-ray reflector is arranged orthogonally to a third direction, wherein the third direction is a bisector of a negative first direction and the second direction.

6. The X-ray apparatus of claim 2, wherein the X-ray-reflector is embodied to focus the X-rays generated by the X-ray source.

7. The X-ray apparatus of claim 6, wherein the X-ray-reflector includes a concave side, embodied to reflect the X-rays generated by the X-ray source.

8. The X-ray apparatus of claim 2, wherein the X-ray-reflector includes at least one of a coated mirror, a multi-layer mirror, and a crystal monochromator.

9. The X-ray apparatus of claim 2, further comprising at least one of a Fresnel zone plate and a refractive X-ray lens.

10. The X-ray apparatus of claim 1, wherein the X-ray-reflector is embodied to focus the X-rays generated by the X-ray source.

11. The X-ray apparatus of claim 10, wherein the X-ray-reflector includes a concave side, embodied to reflect the X-rays generated by the X-ray source.

12. The X-ray apparatus of claim 11, wherein the X-ray-reflector includes at least one of a coated mirror, a multi-layer mirror, and a crystal monochromator.

13. The X-ray apparatus of claim 10, wherein the X-ray-reflector includes at least one of a coated mirror, a multi-layer mirror, and a crystal monochromator.

14. The X-ray apparatus of claim 10, further comprising at least one of a Fresnel zone plate and a refractive X-ray lens.

15. The X-ray apparatus of claim 1, wherein the X-ray-reflector includes at least one of a coated mirror, a multi-layer mirror, and a crystal monochromator.

16. The X-ray apparatus of claim 15, further comprising at least one of a Fresnel zone plate and a refractive X-ray lens.

17. The X-ray apparatus of claim 1, wherein the X-ray-reflector includes a multi-layer mirror, wherein the X-rays generated by the X-ray source are monochromatic, and wherein a layer thickness of the multi-layer mirror is matched to a wavelength of the monochromatic X-rays.

18. The X-ray apparatus of claim 1, further comprising a patient support apparatus, wherein the patient support apparatus is arranged in a beam path of the X-rays between the X-ray reflector and the X-ray detector.

19. The X-ray apparatus of claim 1, further comprising at least one of a Fresnel zone plate and a refractive X-ray lens.

20. An X-ray apparatus, comprising:
    an X-ray source embodied to generate X-rays;
    an X-ray detector;
    an X-ray-reflector, embodied to reflect the X-rays generated by the X-ray source such that reflected X-rays hit the X-ray detector; and
    at least one of a Fresnel zone plate and a refractive X-ray lens.

21. The X-ray apparatus of claim 20, further comprising a patient support apparatus arranged in a beam path of the X-rays, generated by the X-ray source, between the X-ray reflector and the X-ray detector.

22. A method for operating an X-ray apparatus, comprising:
    receiving an examination region;
    generating X-rays via an X-ray source of the X-ray apparatus;
    first setting of at least one of a position and an orientation of an X-ray reflector of the X-ray apparatus so that the X-rays generated by the X-ray source are reflected by the X-ray-reflector to irradiate the examination region; and
    detecting the X-rays via an X-ray detector of the X-ray apparatus, wherein
    the X-ray reflector and the X-ray detector are rotatable simultaneously about at least one of a common first axis of rotation; and
    a common second axis of rotation.

23. The method of claim 22, wherein the first setting of at least one of the position and the orientation of the X-ray-reflector of the X-ray apparatus includes first setting of the at least one of the position and the orientation of the X-ray reflector of the X-ray apparatus such that an angle of reflection of the X-rays generated by the X-ray source corresponds to a specified angle of reflection.

24. The method of claim 23, further comprising:
    second setting of at least one of a position and an orientation of the X-ray detector of the X-ray apparatus so that the X-ray detector is arranged orthogonally to the X-rays reflected by the X-ray-reflector.

25. The method of claim 22, further comprising:
    second setting of at least one of a position and an orientation of the X-ray detector of the X-ray apparatus so that the X-ray detector is arranged orthogonally to the X-rays reflected by the X-ray-reflector.

26. A non-transitory computer-readable medium, storing program segments downloadable and executable by a processor, to perform the method of claim 22, when the program segments are executed by the processor.

27. A non-transitory computer-readable medium, storing program segments downloadable and executable by a processor, to perform the method of claim 25, when the program segments are executed by the processor.

* * * * *